US012285419B2

(12) United States Patent
Garcia et al.

(10) Patent No.: US 12,285,419 B2
(45) Date of Patent: Apr. 29, 2025

(54) BUPIVACAINE MULTIVESICULAR LIPOSOME FORMULATIONS AND USES THEREOF

(71) Applicant: Pacira Pharmaceuticals, Inc., San Diego, CA (US)

(72) Inventors: Louie D. Garcia, San Diego, CA (US); Soroush M. Ardekani, San Diego, CA (US); Paige N. Davis, San Diego, CA (US); Stephanie M. Kurz, San Diego, CA (US); Damon A. Leon, San Diego, CA (US); Kathleen D. A. Los, San Diego, CA (US); John J. Grigsby, Jr., San Diego, CA (US); Eran Levy, San Diego, CA (US); Alisha R. Simonian, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 18/046,416

(22) Filed: Oct. 13, 2022

(65) Prior Publication Data

US 2023/0133849 A1 May 4, 2023

Related U.S. Application Data

(60) Provisional application No. 63/255,690, filed on Oct. 14, 2021.

(51) Int. Cl.
*A61K 31/445* (2006.01)
*A61K 9/127* (2006.01)
*A61K 47/14* (2017.01)
*A61K 47/28* (2006.01)

(52) U.S. Cl.
CPC ............ *A61K 31/445* (2013.01); *A61K 9/127* (2013.01); *A61K 47/14* (2013.01); *A61K 47/28* (2013.01)

(58) Field of Classification Search
CPC ...... A61K 31/445; A61K 9/127; A61K 47/14; A61K 47/28; A61K 9/0019; A61K 9/1277; A61K 9/1278; A61K 47/24
See application file for complete search history.

(56) References Cited

U.S. PATENT DOCUMENTS

| | | |
|---|---|---|
| 3,684,251 A | 8/1972 | Bowling |
| 3,946,994 A | 3/1976 | Mertz et al. |
| 4,026,817 A | 5/1977 | Ciuti et al. |
| 4,078,052 A | 3/1978 | Papahadjopoulos |
| 4,089,801 A | 5/1978 | Schneider |
| 4,113,765 A | 9/1978 | Richardson et al. |
| 4,145,410 A | 3/1979 | Sears |
| 4,224,179 A | 9/1980 | Schneider |
| 4,235,587 A | 11/1980 | Miles |
| 4,235,871 A | 11/1980 | Papahadjopoulos et al. |
| 4,310,506 A | 1/1982 | Baldeschwieler et al. |
| 4,394,372 A | 7/1983 | Taylor |
| 4,420,398 A | 12/1983 | Castino |
| 4,454,083 A | 6/1984 | Brown et al. |
| 4,478,824 A | 10/1984 | Franco et al. |
| 4,522,803 A | 6/1985 | Lenk et al. |
| 4,588,578 A | 5/1986 | Fountain et al. |
| 4,590,030 A | 5/1986 | Gillner et al. |
| 4,599,227 A | 7/1986 | Dees et al. |
| 4,599,342 A | 7/1986 | LaHann |
| 4,610,868 A | 9/1986 | Fountain et al. |
| 4,622,219 A | 11/1986 | Haynes |
| 4,644,056 A | 2/1987 | Kothe et al. |
| 4,652,441 A | 3/1987 | Okada et al. |
| 4,668,580 A | 5/1987 | Dahm et al. |
| 4,711,782 A | 12/1987 | Okada et al. |
| 4,725,442 A | 2/1988 | Haynes |
| 4,744,989 A | 5/1988 | Payne et al. |
| 4,752,425 A | 6/1988 | Martin et al. |
| 4,761,255 A | 8/1988 | Dahm et al. |
| 4,761,288 A | 8/1988 | Mezei |
| 4,769,250 A | 9/1988 | Forssen |
| 4,776,991 A | 10/1988 | Farmer et al. |
| 4,781,831 A | 11/1988 | Goldsmith |
| 4,781,871 A | 11/1988 | West, III et al. |
| 4,788,001 A | 11/1988 | Narula |
| 4,844,620 A | 7/1989 | Lissant et al. |
| 4,844,904 A | 7/1989 | Hamaguchi et al. |

(Continued)

FOREIGN PATENT DOCUMENTS

| | | |
|---|---|---|
| CA | 2078666 | 9/1991 |
| CA | 1323568 | 10/1993 |

(Continued)

OTHER PUBLICATIONS

"Guidance for Industry: Guideline on Sterile Drug Products Produced by Aseptic Processing," Jun. 1987, Reprinted Jun. 1991, pp. 1-43, Center for Drug Evaluation and Research et al.
"Local Anesthetics," New Pharmacology, Revised 3.sup.rd ed., pp. 261-266, Tanaka et al. eds. Nankoudou Corp., Aug. 1, 1997.
Sep. 30, 2021 Bupivacaine liposome injectable suspension ANDA No. 214348, Paragraph IV Notice Letter Invalidity contentions for U.S. Pat. No. 11,033,495.
Dec. 28, 2021 Redacted Bupivacaine liposome injectable suspension ANDA No. 214348, Paragraph IV Notice Letter Invalidity contentions for U.S. Pat. No. 11,179,336.

(Continued)

*Primary Examiner* — Walter E Webb
(74) *Attorney, Agent, or Firm* — Knobbe Martens Olson & Bear LLP

(57) ABSTRACT

Some embodiments of the present application are related to multivesicular liposome formulations comprising high concentration of bupivacaine for the purpose of preventing, treating or ameliorating pain, for example, post-surgical pain for an extended period of time. Processes of making and administering bupivacaine encapsulated multivesicular liposome formulations (BUP-MVLs) and their uses as medicaments are also provided.

38 Claims, 1 Drawing Sheet

(56) References Cited

U.S. PATENT DOCUMENTS

| | | | |
|---|---|---|---|
| 4,861,597 A | 8/1989 | Kida et al. |
| 4,877,561 A | 10/1989 | Iga et al. |
| 4,877,619 A | 10/1989 | Richer |
| 4,908,463 A | 3/1990 | Bottelberghe |
| 4,920,016 A | 4/1990 | Allen et al. |
| 4,921,644 A | 5/1990 | Lau et al. |
| 4,921,853 A | 5/1990 | LeBlanc |
| 4,937,078 A | 6/1990 | Mezei et al. |
| 4,946,683 A | 8/1990 | Forssen |
| 4,956,290 A | 9/1990 | Harrison et al. |
| 5,000,959 A | 3/1991 | Iga et al. |
| 5,004,611 A | 4/1991 | Leigh |
| 5,013,556 A | 5/1991 | Woodle et al. |
| 5,019,394 A | 5/1991 | Hamaguchi et al. |
| 5,021,200 A | 6/1991 | Vanlerberghe et al. |
| 5,049,392 A | 9/1991 | Weiner et al. |
| 5,069,936 A | 12/1991 | Yen |
| 5,077,056 A | 12/1991 | Bally et al. |
| 5,091,187 A | 2/1992 | Haynes |
| 5,094,854 A | 3/1992 | Ogawa et al. |
| 5,100,591 A | 3/1992 | Leclef et al. |
| 5,141,674 A | 8/1992 | Leigh |
| 5,147,134 A | 9/1992 | Bradley et al. |
| 5,169,637 A | 12/1992 | Lenk et al. |
| 5,186,941 A | 2/1993 | Callahan et al. |
| 5,192,549 A | 3/1993 | Barenolz et al. |
| 5,204,112 A | 4/1993 | Hope et al. |
| 5,211,955 A | 5/1993 | Legros et al. |
| 5,225,212 A | 7/1993 | Martin et al. |
| 5,227,165 A | 7/1993 | Domb et al. |
| 5,227,170 A | 7/1993 | Sullivan |
| 5,244,678 A | 9/1993 | Legros et al. |
| 5,246,707 A | 9/1993 | Haynes |
| 5,261,903 A | 11/1993 | Dhaliwal et al. |
| 5,292,701 A | 3/1994 | Glemza et al. |
| 5,321,012 A | 6/1994 | Mayer et al. |
| 5,334,381 A | 8/1994 | Unger |
| 5,334,391 A | 8/1994 | Clark et al. |
| 5,364,632 A | 11/1994 | Benita et al. |
| 5,387,387 A | 2/1995 | James et al. |
| 5,393,530 A | 2/1995 | Schneider et al. |
| 5,407,660 A | 4/1995 | Bosworth et al. |
| 5,415,867 A | 5/1995 | Minchey et al. |
| 5,422,120 A | 6/1995 | Kim |
| 5,451,408 A | 9/1995 | Mezei et al. |
| 5,455,044 A | 10/1995 | Kim et al. |
| RE35,192 E | 3/1996 | Reese |
| 5,533,526 A | 7/1996 | Goldberg |
| 5,543,158 A | 8/1996 | Gref et al. |
| 5,576,017 A | 11/1996 | Kim |
| 5,576,018 A | 11/1996 | Kim et al. |
| 5,589,189 A | 12/1996 | Moynihan |
| 5,635,205 A | 6/1997 | Nyqvist et al. |
| 5,658,898 A | 8/1997 | Weder et al. |
| 5,662,931 A | 9/1997 | Munechika et al. |
| 5,681,464 A | 10/1997 | Larsson |
| 5,700,482 A | 12/1997 | Frederiksen et al. |
| 5,708,011 A | 1/1998 | Bardsley et al. |
| 5,723,147 A | 3/1998 | Kim et al. |
| 5,766,627 A | 6/1998 | Sankaram et al. |
| 5,770,222 A | 6/1998 | Unger et al. |
| 5,776,486 A | 7/1998 | Castor et al. |
| 5,776,915 A | 7/1998 | Peterson et al. |
| 5,807,573 A | 9/1998 | Ljusberg-Wahren et al. |
| 5,814,335 A | 9/1998 | Webb et al. |
| 5,827,533 A | 10/1998 | Needham |
| 5,837,282 A | 11/1998 | Fenske et al. |
| 5,849,763 A | 12/1998 | Bardsley et al. |
| 5,853,755 A | 12/1998 | Foldvari |
| 5,865,184 A | 2/1999 | Takiguchi |
| 5,879,672 A | 3/1999 | Davis et al. |
| 5,882,679 A | 3/1999 | Needham |
| 5,885,260 A | 3/1999 | Mehl, Sr. et al. |
| 5,891,467 A | 4/1999 | Willis |
| 5,891,842 A | 4/1999 | Kream |
| 5,895,661 A | 4/1999 | Tournier et al. |
| 5,910,502 A | 6/1999 | Gennery |
| 5,912,271 A | 6/1999 | Brodin et al. |
| 5,919,804 A | 7/1999 | Gennery |
| 5,922,340 A | 7/1999 | Berde et al. |
| 5,942,253 A | 8/1999 | Gombotz et al. |
| 5,945,126 A | 8/1999 | Thanoo et al. |
| 5,945,435 A | 8/1999 | Evetts |
| 5,947,689 A | 9/1999 | Schick |
| 5,948,441 A | 9/1999 | Lenk et al. |
| 5,955,087 A | 9/1999 | Whittle et al. |
| 5,955,479 A | 9/1999 | Bardsley et al. |
| 5,962,016 A | 10/1999 | Willis |
| 5,962,532 A | 10/1999 | Campbell et al. |
| 5,977,326 A | 11/1999 | Scheinmann et al. |
| 5,980,927 A | 11/1999 | Nelson et al. |
| 5,980,937 A | 11/1999 | Tournier et al. |
| 5,997,899 A | 12/1999 | Ye et al. |
| 6,007,838 A | 12/1999 | Alving et al. |
| 6,033,708 A | 3/2000 | Kwasiborski et al. |
| 6,045,824 A | 4/2000 | Kim et al. |
| 6,046,187 A | 4/2000 | Berde et al. |
| 6,048,545 A | 4/2000 | Keller et al. |
| 6,066,331 A | 5/2000 | Barenholz et al. |
| 6,069,155 A | 5/2000 | Mather et al. |
| 6,071,534 A | 6/2000 | Kim et al. |
| 6,103,741 A | 8/2000 | Bardsley et al. |
| 6,106,858 A | 8/2000 | Ye et al. |
| 6,120,797 A | 9/2000 | Meers et al. |
| 6,132,766 A | 10/2000 | Sankaram et al. |
| 6,149,937 A | 11/2000 | Camu et al. |
| 6,171,613 B1 | 1/2001 | Ye et al. |
| 6,193,998 B1 | 2/2001 | Ye et al. |
| 6,217,899 B1 | 4/2001 | Benameur et al. |
| 6,221,385 B1 | 4/2001 | Camu et al. |
| 6,221,401 B1 | 4/2001 | Zasadzinski et al. |
| 6,238,702 B1 | 5/2001 | Berde et al. |
| 6,241,999 B1 | 6/2001 | Ye et al. |
| 6,264,988 B1 | 7/2001 | Yen |
| 6,270,802 B1 | 8/2001 | Thanoo et al. |
| 6,287,587 B2 | 9/2001 | Shigeyuki et al. |
| 6,306,432 B1 | 10/2001 | Shirley et al. |
| 6,355,267 B1 | 3/2002 | Collins |
| 6,399,094 B1 | 6/2002 | Brandl et al. |
| 6,417,201 B1 | 7/2002 | Bardsley et al. |
| 8,182,835 B2 | 5/2012 | Kim et al. |
| 8,834,921 B2 | 9/2014 | Kim et al. |
| 9,192,575 B2 | 11/2015 | Kim et al. |
| 9,205,052 B2 | 12/2015 | Kim et al. |
| 9,585,838 B2 | 3/2017 | Hartounian et al. |
| 9,730,892 B2 | 7/2017 | Schutt et al. |
| 10,398,648 B2 | 9/2019 | Schutt |
| 10,449,152 B2 * | 10/2019 | Ohri ................. A61P 29/00 |
| 10,842,745 B2 | 11/2020 | Barenholz et al. |
| 11,033,495 B1 | 6/2021 | Hall et al. |
| 11,185,506 B1 | 11/2021 | Hall et al. |
| 11,179,336 B1 | 12/2021 | Hall et al. |
| 11,278,494 B1 | 3/2022 | Hall et al. |
| 11,304,904 B1 | 4/2022 | Hall et al. |
| 11,311,486 B1 | 4/2022 | Hall et al. |
| 11,357,727 B1 | 6/2022 | Hall et al. |
| 11,426,348 B2 | 8/2022 | Hall et al. |
| 11,452,691 B1 | 9/2022 | Hall et al. |
| 11,925,706 B2 | 3/2024 | Hall et al. |
| 2002/0039596 A1 | 4/2002 | Hartounian et al. |
| 2002/0041895 A1 | 4/2002 | Gregoriadis et al. |
| 2003/0201230 A1 | 10/2003 | Kopf |
| 2004/0247659 A1 | 12/2004 | Eibl |
| 2011/0244029 A1 * | 10/2011 | Barenholz ........... A61K 31/573 424/450 |
| 2011/0250264 A1 | 10/2011 | Schutt et al. |
| 2013/0183375 A1 | 7/2013 | Schutt |
| 2013/0189350 A1 | 7/2013 | Garcia et al. |
| 2013/0251786 A1 | 9/2013 | Li |
| 2014/0004173 A1 | 1/2014 | Hartounian et al. |
| 2014/0319045 A1 | 10/2014 | Shevitz |
| 2015/0158907 A1 | 6/2015 | Zhou |
| 2018/0161275 A1 | 6/2018 | Los et al. |
| 2019/0169559 A1 | 6/2019 | Coffman |

(56) References Cited

U.S. PATENT DOCUMENTS

| | | |
|---|---|---|
| 2019/0314281 A1 | 10/2019 | Ma et al. |
| 2022/0233447 A1 | 7/2022 | Hall et al. |
| 2022/0233448 A1 | 7/2022 | Hall et al. |
| 2022/0304932 A1 | 9/2022 | Hall et al. |
| 2023/0248648 A1 | 8/2023 | Hall et al. |
| 2023/0301916 A1 | 9/2023 | Hall et al. |

FOREIGN PATENT DOCUMENTS

| | | |
|---|---|---|
| CA | 2176712 | 5/1995 |
| CA | 1337273 | 10/1995 |
| CA | 2199004 | 5/2000 |
| CN | 110179752 A | 8/2019 |
| CN | 108078929 B | 1/2021 |
| EP | 0 126 580 | 11/1984 |
| EP | 0 208 450 | 1/1987 |
| EP | 0 506 639 | 9/1992 |
| EP | 0 280 503 | 4/1993 |
| EP | 0 752 245 | 1/1997 |
| EP | 3 572 070 | 11/2019 |
| GB | 2050287 | 1/1981 |
| WO | WO 85/03011 | 7/1985 |
| WO | WO 89/00846 | 2/1989 |
| WO | WO 89/04656 | 6/1989 |
| WO | WO 91/14445 | 10/1991 |
| WO | WO 93/00888 | 1/1993 |
| WO | WO 94/08565 | 4/1994 |
| WO | WO 94/08626 | 4/1994 |
| WO | WO 94/22430 | 10/1994 |
| WO | WO 94/23697 | 10/1994 |
| WO | WO 94/26250 | 11/1994 |
| WO | WO 94/26253 | 11/1994 |
| WO | WO 94/27581 | 12/1994 |
| WO | WO 95/01164 | 1/1995 |
| WO | WO 95/13796 | 5/1995 |
| WO | WO 96/08235 | 3/1996 |
| WO | WO 96/14057 | 5/1996 |
| WO | WO 97/02022 | 1/1997 |
| WO | WO 97/03652 | 6/1997 |
| WO | WO 97/35561 | 10/1997 |
| WO | WO 98/014171 | 4/1998 |
| WO | WO 98/033483 | 8/1998 |
| WO | 99/12523 * | 3/1999 |
| WO | 99/13865 * | 3/1999 |
| WO | WO 12/109387 | 8/2012 |
| WO | WO 21/11299 | 1/2021 |

OTHER PUBLICATIONS

Andrews et al., "Boundary Layer Solution for a Bubble Rising Through a Liquid Containing Surface-Active Contaminants," Ind. Eng. Chem. Res., 1995, 34(4):1371-1382.
Arroyo et al., "Use of intermittent jets to enhance flux in crossflow filtration," J. Membrane Sci., 1993, 80:117-129.
Assil et al., "Liposome Suppression of Proliferative Vitreoretinopathy: Rabbit Model Using Antimetabolite Encapsulated Liposomes," Invest. Ophthalmol. Vis. Sci., 32(11):2891-2897, 1991.
Assil et al., "Multivesicular Liposomes: Sustained Release of the Antimetabolite Cytarabine in the Eye," Arch Ophthalmol., 1987, 105(3):400-403.
Assil et al., "Tobramycin Liposomes: Single Subconjunctival Therapy of Pseudomonal Keratitis," Invest. Ophthalmol. Vis. Sci., 32(13):3216-3220, 1991.
Bangham et al., "Diffusion of Univalent Ions Across the Lamellae of Swollen Phospholipids," J. Mol. Biol., 1965, 13:238-252.
Barbet et al., "Weak acid-induced release of liposome-encapsulated carboxyfluorescein," Biochim. Biophys. Acta, 1984, 772:347-356.
Bhave, "Cross-Flow Filtration," Fermentation and Biochemical Engineering Handbook: Principles, Process Design and Equipment, 2.sup.nd edition, (Vogel et al. Eds., 1997), Noyes Publications, Westwood, New Jersey, pp. 271-278.
Bonetti et al., "An extended-release formulation of methotrexate for subcutaneous administration," Cancer Chemother. Pharmacol., 33:303-306, 1994.
Boogaerts et al. "Biodistribution of liposome-associated bupivacaine after extradural administration to rabbits," Br. J. Anaesth, 1995, 75:319-325.
Boogaerts et al. "Epidural Administration of Liposome-Associated Bupivacaine for the Management of Postsurgical Pain: A First Study," J. Clin. Anesth, 1994, 6:315-320.
Boogaerts et al. "Motor Blockade and Absence of Local Nerve Toxicity Induced by Liposomal Bupivacaine Injected into the Axillary Plexus of Rabbits," Acta Anesth. Belg., 1995, 46:19-24.
Boogaerts et al. "Plasma concentrations of bupivacaine after brachial plexus administration of liposome-associated and plain solutions to rabbits," Can. J. Anaesth, 1993, 40:1201-1204.
Boogaerts et al. "Toxicity of Bupivacaine Encapsulated into Liposomes and Injected Intravenously: Comparison with Plan Solutions," Anesth. Analg., 1993, 76:553-555.
Chamberlain et al., "Treatment of Leptomeningeal Metastasis With Intraventricular Administration of Depot Cytarabine (DTC 101): A Phase I Study," Arch. Neurol., 50:261-264, 1993.
Chatelut et al., "A slow-release methotrexate formulation for intrathecal chemotherapy," Cancer Chemother. Pharmacol., 32:179-182, 1993.
Chattopadhyay et al., "The Protective Effect of Specific Medium Additives with Respect to Bubble Rupture," Biotechnol. Bioeng., 1995, 45(6):473-480.
Chemical Comprehensive Dictionary, compact 2.sup.rd ed., Kyoritsushuppan Corp., edited by the Editorial Committee of the Chemical Comprehensive Dictionary, Aug. 25, 1963, pp. 725-726.
Cherry et al., "Cell Death in the Thin Films of Bursting Bubbles," Biotechnol. Prog., 1992, 8(1):11-18.
Cullis et al., "Structural Properties and Functional Roles of Phospholipids in Biological Membranes," Phospholipids and Cellular Regulation, pp. 1-59, vol. 1, J.F. Kuo ed., CRC Press, 1985, Boca Raton, FL.
Davidson et al., 2010, High-dose bupivacaine remotely loaded into multivesicular liposomes demonstrates slow drug release without systemic toxic plasma concentrations after subcutaneous administration in humans, Anethesia & Analgesia, 110(4):1018-1023.
De Gier, J et al., Lipid Composition and Permeability of Liposomes, Biochim. Biophys. Acta 150:666-675 (1968).
Edwards et al., "Large Porous Particles for Pulmonary Drug Delivery," Science, 1997, 276: 1868-1871.
Frucht-Perry et al., "Fibrin-Enmeshed Tobramycin Liposomes: Single Application Topical Therapy of Pseudomonas Keratitis," Cornea, 1992, 11(5):393-397.
Genovesi, "Several uses for tangential-flow filtration in the pharmaceutical industry," J. Parenter. Sci. Technol. (1983), 37(3):81-86.
Grit et al., Apr. 1993, Hydrolysis of saturated soybean phosphatidylcholine in aqueous liposome dispersions, Journal of Pharmaceutical Sciences, 82(4):362-366.
Gruner et al., "Novel Multilayered Lipid Vesicles: Comparison of Physical Characteristics of Multilamellar Liposomes and Stable Plurilamellar Vesicles," Biochemistry, 1985, 24(12):2833-2842.
Holdich et al., "The variation of crossflow filtration rate with wall shear stress and the effect of deposit thickness," Chemical Engineering Research and Design (Trans IChem), 1995, 73(part A):20-26.
Huang, "Studies on Phosphatidylcholine Vesicles. Formation and Physical Characteristics," Biochemistry, 1969, 8(1):344-352.
Huang, et al., "Determination of phospholipid and fatty glyceride in liposome by RP-HPLC with capacitively coupled contactless conductivity detector," Analytical Methods, 2018, 10, 4978-4984.
Ishii, "Production and size control of large unilamellar liposomes by emulsification," Liposome Technology 2.sup.nd Edition, pp. 111-121, vol. 1, Gregory Gregoriadis ed., CRC Press, 1993, Boca Raton, FL.
Jaffrin et al., "Energy saving pulsatile mode cross flow filtration," J. Membrane Sci., 1994, 86:281-290.
Johnson et al., "New nozzle improves FCC feed atomization, unit yield patterns," Oil and Gas Journal, 1994, 92(3):80-86.

(56) References Cited

OTHER PUBLICATIONS

Joshi et al., "The safety of liposome bupivacaine following various routes of administration in animals" J. Pain. Res., 8, 781-789 (2015).

Kawashima et al., "Shear-Induced Phase Inversion and Size Control of Water/Oil/Water Emulsion Droplets with Porous Membrane," J. Colloid Interface Sci., 1991, 145(2):512-523.

Kim "Liposomes as Carriers of Cancer Chemotherapy: Current status and Future Prospects," Drugs, 46(4):618-638,1993.

Kim et al., "Direct Cerebrospinal Fluid Delivery of an Antiretroviral Agent Using Multivesicular Liposomes," J. Infect. Dis., 1990, 162(3):750-752.

Kim et al., "Extended CSF Cytarabine Exposure Following Intrathecal Administration of DTC 101," J. Olin. Oncol., 1993, 11(11):2186-2193.

Kim et al., "Extended-release formulation of morphine for subcutaneous administration," Cancer Chemother. Pharmacol., 1993, 33(3):187-190.

Kim et al., "Modulation of the peritoneal clearance of liposomal cytosine arabinoside by blank liposomes," Cancer Chemother. Pharmacol., 1987, 19(4):307-310.

Kim et al., "Multivesicular Liposomes Containing 1-beta-D-Arabinofuranosylcytosine for Slow-Release Intrathecal Therapy," Cancer Res., 47(15):3935-3937, 1987.

Kim et al., "Multivesicular Liposomes Containing Cytarabine Entrapped in the Presence of Hydrochloric Acid for Intracavitary Chemotherapy," Cancer Treat. Rep., 71(7-8):705-711, 1987.

Kim et al., "Multivesicular Liposomes Containing Cytarabine for Slow-Release Sc Administration," Cancer Treat. Rep., 71(5):447-450, 1987.

Kim et al., "Preparation of cell-size unilamellar liposomes with high captured volume and defined size distribution," Biochim. Biophys. Acta, 1981, 646:1-9.

Kim et al., "Preparation of multilamellar vesicles of defined size-distribution by solvent-spherule evaporation," Biochim. Biophys. Acta, 1985, 812:793-801.

Kim et al., "Preparation of Multivesicular Liposomes," Biochim. Biophys. Acta, 728(3):339-348, 1983.

Kim et al., "Prolongation of Drug Exposure in Cerebrospinal Fluid by Encapsulation into DepoFoam," Cancer Res., 53(7):1596-1598, 1993.

Kim, T. et al., "Extended-release formulations of morphine for subcutaneous administration," Cancer Chemother. Pharmacol., vol. 33, pp. 187-190 (1993).

Lafont et al. "Use of Liposome-Associated Bupivacaine for the Management of a Chronic Pain Syndrome," Anesth. Analg., 1994, 79:818.

Lafont et al. "Use of Liposome-Associated Bupivacaine in a Cancer Pain Syndrome," Anaesthesia, 1996, 51:578-579.

Legros et al. "Influence of Different Liposomal Formulations on the Pharmacokinetics of Encapsulated Bupivacaine," [Abstract]. Anesthesiology, 1990, 73: A851.

Liposome Drug Products. Chemistry, Manufacturing, and Controls; Human Pharmacokinetics and Bioavailability; and Labeling Documentation. Guidance for Industry, U.S. Department of Health and Human Services, Food and Drug Administration, Center for Drug Evaluation and Research (CDER), Apr. 2018.

Maa et al., "Liquid-liquid emulsification by rotor/stator homogenization," J. Controlled Release, 1996, 38:219-228.

Maestre et al., "Contribution of Light Scattering to the Circular Dichroism of Deoxyribonucleic Acid Films, Deoxyribonucleic Acid-Polylysine Complexes, and Deoxyribonucleic Acid Particles in Ethanolic Buffers," Biochemistry, 1980, 19(23):5214-5223.

Malinovsky et al., "Neurotoxilogical Assessment After Intracisternal Injection of Liposomal Bupivacaine in Rabbits," Anesth. Analg., 1997, 85:1331-1336.

Mancini, "Mastering the mix: Why Leave Mixing to Chance? Get a Proper Mix and a Better Product Every Time," Food Engineering, Mar. 1996, pp. 79-83.

Maranges et al., "Crossflow Filtration of *Saccharomyces cerevisiae* Using an Unsteady Jet," Biotechnol. Tech., 1995, 9(9): 649-654.

Mashimo et al. "Prolongation of Canine Epidural Anesthesia by Liposome Encapsulation of Lidocaine," Anesth. Analg., 1992, 74:827-834.

Matsumoto et al., "An Attempt at Preparing Water-in-Oil-in-Water Multiple-Phase Emulsions," J. Colloid Interface Sci., 1976, 57(2):353-361.

Meissner, D., et al., Application of High Frequency Backpulsing in Diafiltration of Multivesicular Liposomes, North American Membrane Society, Proceedings, 9.sup.th Annual Meeting, May 31-Jun. 4, 1997, Baltimore, MD, (1997). Abstract.

Meissner, D., et al., Application of Unsteady Flow Patterns in Permeate and Retentate for the Diafiltration of Multivesicular Lipid Based Particles, Annual AIChE Meeting, Nov. 16-21, 1997, Los Angeles, CA. Unpublished conference paper (1997). Linda Hall Library, Kansas.

Michaels et al., "Sparging and Agitation-Induced Injury of Cultured Animal Cells: Do Cell-to-Bubble Interactions in the Bulk Liquid Injure Cells?" Biotechnol. Bioeng., 1996, 51(4):399-409.

Mutsakis et al., "Advances in Static Mixing Technology," Chem. Eng. Prog, Jul. 1986, pp. 42-48.

Narhi et al., "Role of Native Disulfide Bonds in the Structure and Activity of Insulin-like Growth Factor 1: Genetic Models of Protein-Folding Intermediates," Biochemistry, 1993, 32(19):5214-5221.

Pacira Pharmaceuticals Inc., 2018, Exparel prescribing information, 28 pp.

Paul, "Reaction Systems for Bulk Pharmaceutical Production," Chem. Ind., May 21, 1990, pp. 320-325.

Quirk et al., "Investigation of the parameters affecting the separation of bacterial enzymes from cell debris by tangential flow filtration," Enzyme Microb. Technol. (1984), 6(5):201-206.

Radlett, "The Concentration of Mammalian Cells in a Tangential Flow Filtration Unit," J. Appl. Chem. Biotechnol. (1972), 22:495-499.

Redkar et al., "Cross-Flow Microfiltration with High-Frequency Reverse Filtration," AIChE Journal, 1995, 41(3):501-508.

Richard et al., 2011, The safety and tolerability evaluation of DepoFoam, bupivacaine (bupivacaine extended-relase liposome injection) administered by incision would infltration in rabbits and dogs, Expert Opinion on Investigational Drugs, 20(10):1327-1341.

Ripperger, et al., "Crossflow microfiltration—state of the art," Separation and Purification Technology, 26 (2002), 19-31.

Rodgers et al., "Reduction of Membrane Fouling in the Ultrafiltration of Binary Protein Mixtures," AIChE Journal, 1991, 37(10):1517-1528.

Roy et al., "Multivesicular liposomes containing bleomycin for subcutaneous administration," Cancer Chemother. Pharmacol., 28(2):105-108, 1991.

Russack et al., "Quantitative Cerebrospinal Fluid Cytology in Patients Receiving Intracavitary Chemotherapy," Ann. Neurol., 1993, 34(1):108-112.

Saberi et al., "Bubble Size and Velocity Measurement in Gas-Liquid Systems: Application of Fiber Optic Technique to Pilot Plant Scale," Can. J. Chem. Eng., 1995, 73: 253-257.

Shakiba et al., "Evaluation of Retinal Toxicity and Liposome Encapsulation of the Anti-CMV drug 2'-nor-cyclic GMP," Invest. Ophthalmol. Vis. Sci., 34(10):2903-2910, 1993.

Skuta et al., "Filtering Surgery in Owl Monkeys Treated with the Antimetabolite 5-Fluorouridine 5' Monophosphate Entrapped in Multivesicular Liposomes," Am. J. Ophtmalmol., 1987, 103(5):714-716.

Streiff et al., "Don't overlook static-mixer reactors," Chem. Eng., Jun. 1994, pp. 76-82.

Szoka et al., "Comparative properties and methods of preparation of lipid vesicles (liposomes)," Ann. Rev. Biophys. Bioeng., 1980, 9:467-508.

Tanaka et al., "Crossflow Filtration of Baker's Yeast with Periodical Stopping of Permeation Flow and Bubbling," Biotechnol. Bioeng., 1995, 47(3):401-404.

Thompson, G.A. Jr., The Regulation of Membrane Lipid Metabolism 2.sup.nd Ed., CRC Press: Boca Raton, pp. 1-20 (1992).

(56) References Cited

OTHER PUBLICATIONS

Tsuchiya et al., "Tortuosity of Bubble Rise Path in a Liquid-Solid Fluidized Bed: Effect of Particle Shape," AIChE Journal, 1995, 41(6):1368-1374.

Turski et al., "Magnetic Resonance Imaging of Rabbit Brain after Intracarotid Injection of Large Multivesicular Liposomes Containing Paramagnetic Metals and DTPA," Magn. Reson. Med., 7(2):184-196, 1998.

Watts et al., "Microencapsulation Using Emulsification/Solvent Evaporation: An Overview of Techniques and Applications," Critical Reviews in Therapeutic Drug Carrier Systems, 1990, 7(3):235-259.

Zheng et al., "FDA Bioequivalence Standards, Chapter 11, Bioequivalence for Liposomal Drug Products," AAPS Advances in the Pharmaceutical Sciences, vol. 13, 2014, 275-296.

International Search Report and Written Opinion dated Dec. 9, 2022 in International application No. PCT/US2022/046560.

Grit et al., 1993, Chemical stability of liposomes: implications for their physical stability, Chemistry and Physics of Lipids, 64:3-18.

\* cited by examiner

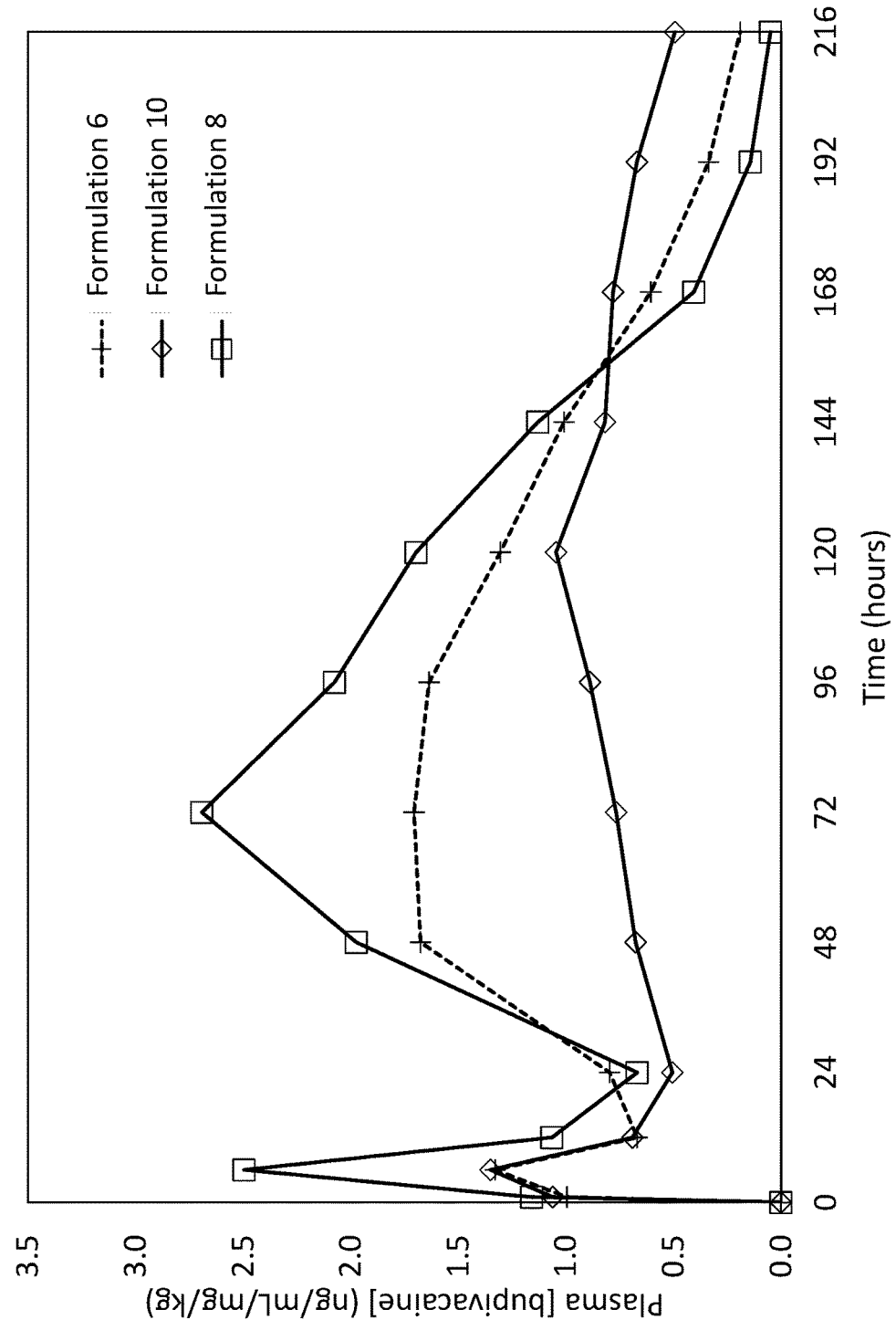

BUPIVACAINE MULTIVESICULAR LIPOSOME FORMULATIONS AND USES THEREOF

BACKGROUND

Field

The present disclosure relates to multivesicular liposome (MVL) formulations of bupivacaine, uses thereof and processes of making the same.

Description of the Related Art

Bupivacaine is a versatile drug that has been shown to be efficacious for pain management in a wide variety of administration routes. It may be used in pre-, intra- and post-operative care settings. Bupivacaine encapsulated multivesicular liposomes (EXPAREL®) has been approved in the US and Europe for use as postsurgical local analgesia and as an interscalene brachial plexus nerve block to produce postsurgical regional analgesia, providing significant long-lasting pain management across various surgical procedures. Particularly, EXPAREL® has had great success in the market in part due to the ability to locally administer bupivacaine multivesicular liposomes (MVLs) at the time of surgery and extend the analgesic effects relative to other non-liposomal formulations of bupivacaine. Such sustained release properties of bupivacaine MVLs allow patients to control their post-operative pain without or with decreased use of opioids. EXPAREL® is a bupivacaine multivesicular liposomal solution comprising 13.3 mg/mL of bupivacaine, which may be used for post-surgical pain management about 2-3 days. For certain post-surgical pain management and chronic pain management, there exists a need for higher dose bupivacaine multivesicular liposomes formulations with a prolonged release time.

SUMMARY

Some aspects of the present disclosure relate to a composition of bupivacaine encapsulated multivesicular liposomes (MVLs), comprising:
  bupivacaine residing inside a plurality of internal aqueous chambers of the MVLs separated by lipid membranes, wherein the lipid membranes comprise at least one amphipathic lipid and at least one neutral lipid; and
  an aqueous medium in which the bupivacaine encapsulated MVLs are suspended;
  wherein the bupivacaine concentration in the composition is from about 18 mg/mL to about 40 mg/mL.

In some embodiments of the composition described herein, the bupivacaine concentration in the composition is about 18 mg/mL, about 19 mg/mL, 20 mg/mL, about 22 mg/mL, about 24 mg/mL, about 26 mg/mL, about 28 mg/mL, about 30 mg/mL, or about 32 mg/mL. In some embodiments, the bupivacaine concentration in the composition is about 18 mg/mL to about 22 mg/mL or about 20 mg/mL. In some embodiments, the composition comprises less than about 10%, 9%, 8%, 7%, 6%, 5%, 4%, 3%, 2%, 1%, 0.9%, 0.8%, 0.7%, 0.6%, 0.5%, 0.4%, 0.3%, or 0.2% by weight of unencapsulated bupivacaine. In some embodiments, the multivesicular liposomes further comprise cholesterol. In some embodiments, the amphipathic lipid comprises a phosphatidylcholine or a salt thereof, a phosphatidylglycerol or a salt thereof, or combinations thereof. In some embodiments, the phosphatidylglycerol is DPPG or a salt thereof (such as sodium salt). In some embodiments, the phosphatidylcholine is selected from the group consisting of DEPC, DSPC, DMPC, DOPC, and salts and combinations thereof. In some embodiments, the neutral lipid comprises triglyceride, propylene glycol ester, ethylene glycol ester, or squalene, or combinations thereof. In some embodiments, the neutral lipid comprises triglyceride. In some embodiments, the triglyceride comprises triolein or tricaprylin, or a combination thereof. In some embodiments, the lipid membrane comprises DPPG or a salt thereof, DEPC, cholesterol, and tricaprylin, and optionally triolein.

In some embodiments of the composition described herein, the plurality of internal aqueous chambers comprise one or more pH modifying agents selected from the group consisting of organic acids, organic bases, inorganic acids, and inorganic bases, and combinations thereof. In some embodiments, the plurality of internal aqueous chambers comprise one or more inorganic acids, or organic acids, or combinations thereof. In some embodiments, the plurality of internal aqueous chambers comprise phosphoric acid or glucuronic acid, or a combination thereof. In some embodiments, the acid to bupivacaine molar ratio in the internal aqueous chambers is from about 0.8:1 to about 1.2:1, or about 1:1. In some embodiments, the plurality of internal aqueous chambers of the MVLs has a pH from about 3.0 to about 6.6. In some embodiments, the plurality of internal aqueous chambers of the MVLs has a pH from about 3.5 to about 6.6.

In some embodiments of the composition described herein, the osmolality of the aqueous medium is from about 280 mOsm/kg to about 500 mOsm/kg. In some embodiments, the osmolality of the aqueous medium is from about 280 mOsm/kg to about 360 mOsm/kg, or about 330 mOsm/kg. In some embodiments, the percent packed particle volume (% PPV) of the bupivacaine encapsulated multivesicular liposomes in the composition is about 35% to 80%, about 40% to 60%, or about 45% to 55%.

In some embodiments of the composition described herein, the aqueous medium comprises at least one buffering agent. In some such embodiments, the buffer agent comprises sodium phosphate. In further embodiments, the concentration of sodium phosphate in the composition is from about 1 mM to about 50 mM, from about 2 mM to about 40 mM, or from about 5 mM to about 20 mM. In one embodiment, the concentration of sodium phosphate in the composition is about 10 mM. In some embodiments, the pH of the aqueous medium is from about 6.0 to about 7.5, from about 6.5 to about 7.5, or about 7.0.

In some embodiments of the composition described herein, the $D_{90}$ of the multivesicular liposomes in the composition is about 30 μm to about 90 km. In some further embodiments, the $D_{90}$ of the multivesicular liposomes in the composition is about 30 μm to about 80 m, about 35 μm to about 75 μm, or about 40 μm to about 70 km.

In some embodiments of the composition described herein, the increase of unencapsulated bupivacaine in the composition is less than about 20%, 15%, 10%, 9%, 8%, 7%, 6%, 5%, 4%, 3%, 2%, or 1% by weight after the composition is stored at 5° C. for six months.

In any embodiments of the composition described herein, bupivacaine is in a salt form. In some embodiment, bupivacaine is in the form of bupivacaine phosphate.

Some additional aspect of the present disclosure relates to a method of treating or ameliorating pain in a subject in need thereof, comprising administering the composition of bupivacaine MVLs to the subject.

In some embodiments of the method described herein, the administration is selected from the group consisting of infiltration, subcutaneous injection, tissue injection, intramuscular injection, spinal injection, intraocular injection, epidural injection, subarachnoid injection, sacroiliac joints injection, intrathecal injection, caudal injection, intraotic injection, and perineural injection, and combinations thereof. In some embodiments, the administration is via local infiltration to a surgical site. In some embodiments, the administration is via a nerve block. For example, the administration is via interscalene brachial plexus nerve block, femoral nerve bloc, sciatic nerve block, or ganglion block. In some embodiments, the method is for treating post-surgical pain. For example, pain associated with cesarean section surgery, bunionectomy, total knee arthroplasty, or oral and maxillofacial procedures. In some embodiments, the pain is chronic pain. In some embodiments, the chronic pain comprises myofascial pain syndromes, complex regional pain syndromes, or radicular back pain. In some embodiments, the Tmax of bupivacaine is from about 6 hours to about 96 hours or from about 6 hours to about 72 hours. In some embodiments, the percent AUC (0-24 hours) of bupivacaine is from about 4% to about 25%%, from about 6% to about 20%, or from about 8% to about 15%. In some embodiments, the total percent AUC is above 90% from 96 hours to about 240 hours, or 192 hours to about 216 hours post administration. In some embodiments, the Cmax of bupivacaine is from about 40 ng/mL to about 100 ng/mL. In some embodiments, the administration provides a sustained release of bupivacaine for about 5 to 15 days, or 8 to 14 days. In some embodiments, the administration provides a sustained release of bupivacaine for about 7, 8, 9, 10, 11 or 12 days.

Some aspects of the present disclosure relate to a process for preparing bupivacaine encapsulated multivesicular liposomes (MVLs), comprising:
  mixing a first aqueous solution with a lipid solution comprising at least one organic solvent, at least one amphipathic lipid, and at least one neutral lipid to form a first water-in-oil emulsion, wherein at least one of the first aqueous solution and the lipid solution comprises bupivacaine;
  combining the first water-in-oil emulsion with a second aqueous solution to form a second emulsion; and
  substantially removing the organic solvent from the second emulsion to form a first aqueous suspension of bupivacaine encapsulated multivesicular liposomes; and
  exchanging the aqueous supernatant of the first aqueous suspension with a third aqueous solution one or more times to provide a final aqueous suspension of bupivacaine encapsulated MVLs, wherein the bupivacaine concentration in the final aqueous suspension is from about 18 mg/mL to about 40 mg/mL.

In some embodiments of the process described herein, the bupivacaine concentration in the final aqueous suspension is about 18 mg/mL, about 19 mg/mL, about 20 mg/mL, about 22 mg/mL, about 24 mg/mL, about 26 mg/mL, about 28 mg/mL, about 30 mg/mL, or about 32 mg/mL. In some embodiments, the first aqueous solution comprises one or more pH modifying agents. In some embodiments, the first aqueous solution comprises one or more inorganic acids, or organic acids, or combinations thereof. In some embodiments, the first aqueous solution comprises phosphoric acid or glucuronic acid, or a combination thereof. In some embodiments, the molar ratio of bupivacaine to the pH adjusting agent in the first aqueous solution is from about 1:1.2 to about 1:2. In some embodiments, bupivacaine is in the lipid solution. In some embodiments, the lipid solution comprises bupivacaine, DPPG or a salt thereof, DEPC, cholesterol, and tricaprylin, and optionally triolein. In some embodiments, unencapsulated bupivacaine is about 10%, 9%, 8%, 7%, 6%, 5%, 4%, 3%, 2%, 1%, 0.9%, 0.8%, 0.7%, 0.6%, 0.5%, 0.4%, 0.3%, 0.2% or less by weight of total amount of bupivacaine in the final aqueous suspension.

In some embodiments of the process described herein, the second aqueous solution comprises one or more tonicity agents and one or more pH modifiers, and the second aqueous solution has an osmolality from about 200 mOsm/kg to about 290 mOsm/kg, or from about 210 mOsm/kg to about 285 mOsm/kg. In some further embodiments, the one or more tonicity agents comprise dextrose. In some further embodiments, the one or more pH modifiers comprise lysine. In some embodiments, the osmolality of the final aqueous suspension of bupivacaine encapsulated MVLs is from about 280 mOsm/kg to about 360 mOsm/kg, about 320 mOsm/kg to about 350 mOsm/kg, or about 330 mOsm/kg.

Additional aspect of the present disclosure relates to a pharmaceutical composition comprising bupivacaine encapsulated multivesicular liposomes prepared by the process described herein.

BRIEF DESCRIPTION OF THE FIGURE

FIG. 1 is a line chart illustrating the dose normalized bupivacaine plasma levels as a function of time, following administration of several bupivacaine encapsulated multivesicular liposomes (BUP-MVLs) compositions.

DETAILED DESCRIPTION

Embodiments of the present disclosure relate to compositions of high concentration and long-lasting bupivacaine encapsulated multivesicular liposomes (MVLs), uses thereof and processes of preparing the same.

Definitions

The section headings used herein are for organizational purposes only and are not to be construed as limiting the subject matter described.

As used herein, the terms "bupivacaine encapsulated multivesicular liposomes", "bupivacaine-MVLs," "bupivacaine MVLs" or "BUP-MVL" refer to a multivesicular liposome composition encapsulating bupivacaine, or a pharmaceutically acceptable salt thereof. In some embodiments, the composition is a pharmaceutical formulation, where the bupivacaine encapsulated multivesicular liposome particles are suspended in a liquid suspending medium (e.g., aqueous medium) to form a suspension. In some such embodiments, the BUP-MVL suspension may also include free or unencapsulated bupivacaine. In some cases, the free or unencapsulated bupivacaine may be less than about 10%, 9%, 8%, 7%, 6%, 5%, 4%, 3%, 2%, 1%, 0.5%, 0.2% or 0.1%, by weight of the total amount of the bupivacaine in the composition, or in a range defined by any of the two preceding values. In some embodiment, the free bupivacaine may be about 5% or less by weight of the total amount of the bupivacaine in the composition. In further embodiments, the free bupivacaine may be about 10% or less during the shelf life of the product (i.e., up to 2 years when stored at 2-8° C.).

As used herein, the term "encapsulated" means that bupivacaine is inside a liposomal particle, for example, the MVL particles. In some instances, bupivacaine may also be on an inner surface, or intercalated in a membrane, of the MVLs.

As used herein, the term "unencapsulated bupivacaine" or "free bupivacaine" refers to bupivacaine or a pharmaceutically acceptable salt thereof outside the liposomal particles, for example the MVL particles. For example, unencapsulated bupivacaine or a salt thereof may reside in the suspending solution of these particles.

As used herein, the term "median particle diameter" refers to volume weighted median particle diameter of a suspension.

As used herein, a "pH adjusting agent" refers to a compound that is capable of modulating the pH of an aqueous phase.

As used herein, the terms "tonicity" and "osmolality" are measures of the osmotic pressure of two solutions, for example, a test sample and water separated by a semi-permeable membrane. Osmotic pressure is the pressure that must be applied to a solution to prevent the inward flow of water across a semi-permeable membrane. Osmotic pressure and tonicity are influenced only by solutes that cannot readily cross the membrane, as only these exert an osmotic pressure. Solutes able to freely cross the membrane do not affect tonicity because they will become equal concentrations on both sides of the membrane. An osmotic pressure provided herein is as measured on a standard laboratory vapor pressure or freezing point osmometer.

As used herein, the term "sugar" as used herein denotes a monosaccharide or an oligosaccharide. A monosaccharide is a monomeric carbohydrate which is not hydrolysable by acids, including simple sugars and their derivatives, e.g., aminosugars. Examples of monosaccharides include sorbitol, glucose, fructose, galactose, mannose, sorbose, ribose, deoxyribose, dextrose, neuraminic acid. An oligosaccharide is a carbohydrate consisting of more than one monomeric saccharide unit connected via glycosidic bond(s) either branched or in a chain. The monomeric saccharide units within an oligosaccharide can be the same or different. Depending on the number of monomeric saccharide units the oligosaccharide is a di-, tri-, tetra-, penta- and so forth saccharide. In contrast to polysaccharides, the monosaccharides and oligosaccharides are water soluble. Examples of oligosaccharides include sucrose, trehalose, lactose, maltose and raffinose.

As used herein, the term "amphipathic lipids" include those having a net negative charge, a net positive charge, and zwitterionic lipids (having no net charge at their isoelectric point).

As used herein, the term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are multiple definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Bupivacaine Multivesicular Liposomes Compositions

MVLs are a group of unique forms of synthetic membrane vesicles that are different from other lipid-based delivery systems such as unilamellar liposomes and multilamellar liposomes (Bangham, et al., J Mol. Bio., 13:238-252, 1965). The main structural difference between multivesicular liposomes and unilamellar liposomes (also known as unilamellar vesicles, "ULVs"), is that multivesicular liposomes contain multiple internal aqueous chambers per particle. The main structural difference between multivesicular liposomes and multilamellar liposomes (also known as multilamellar vesicles, "MLVs"), is that in multivesicular liposomes the multiple internal aqueous chambers are non-concentric. Multivesicular liposomes generally have between 100 to 1 million chambers per particle and all the internal chambers are interconnected by shared lipid-bilayer walls that separate the chambers. The structural differences between unilamellar, multilamellar, and multivesicular liposomes are illustrated in Sankaram et al., U.S. Pat. Nos. 5,766,627 and 6,132,766.

The structural and functional characteristics of multivesicular liposomes are not directly predictable from current knowledge of unilamellar vesicles and multilamellar vesicles. Multivesicular liposomes have a very distinctive internal morphology, which may arise as a result of the special method employed in the manufacture. Topologically, multivesicular liposomes are defined as having multiple non-concentric chambers within each particle, resembling a "foam-like" or "honeycomb-like" matrix; whereas multilamellar vesicles contain multiple concentric chambers within each liposome particle, resembling the "layers of an onion."

The presence of internal membranes distributed as a network throughout multivesicular liposomes may serve to confer increased mechanical strength to the vesicle. The particles themselves can occupy a very large proportion of the total composition volume. The packed particle volume (PPV) of MVLs which is measured in a manner analogous to a hematocrit, representing the volume of the composition that the particles make up and can approach as high as 80%. Typically, the PPV is about 35 to 60%. At 50% PPV, the multivesicular liposome composition typically consists of less than 5% w/w lipid. Thus, the encapsulated volume is approximately 50% while having a relatively low lipid concentration. The multivesicular nature of multivesicular liposomes also indicates that, unlike for unilamellar vesicles, a single breach in the external membrane of multivesicular vesicles will not result in total release of the internal aqueous contents.

Thus, multivesicular liposomes compositions consist of microscopic, spherical particles composed of numerous nonconcentric internal aqueous chambers. The individual chambers are separated by lipid bilayer membranes composed of synthetic versions of naturally occurring lipids, resulting in a delivery vehicle that is both biocompatible and biodegradable. Thus, BUP-MVL compositions include microscopic, spherical particles composed of numerous nonconcentric internal aqueous chambers encapsulating bupivacaine for controlled release drug delivery. Such composition is intended to prolong the local delivery of bupivacaine, thereby enhancing the duration of action of the reduction of pain. The BUP-MVL formulation or composition provides either local site or systemic sustained delivery, and can be administered by a number of routes including subcutaneous, intraarticular into joints, intramuscular into muscle tissue, intraperitoneal, intrathecal, or application to an open wound, or body cavities such as the nasal cavity.

Some embodiments of the present application relate to compositions of high potency bupivacaine encapsulated multivesicular liposomes (MVLs) that provide a longer sustained release profile than Exparel®. The bupivacaine MVL compositions described herein are designed to provide a longer pain relief in areas that repeated injections are undesirable or difficult to administer (e.g., spinal injection, epidural injection, intrathecal injection, etc.) The compositions include bupivacaine residing inside a plurality of internal aqueous chambers of the MVLs separated by lipid membranes, wherein the lipid membranes comprise at least one amphipathic lipid and at least one neutral lipid, and an aqueous medium in which the bupivacaine encapsulated MVLs are suspended. In some embodiment, the bupivacaine concentration in the composition is at least about 18 mg/mL, for example, is from about 18 mg/mL to about 40 mg/mL. In further embodiments, the bupivacaine concentration in the composition in about 18 mg/mL to about 24 mg/mL or about 20 mg/mL. In some embodiments, the composition comprises unencapsulated bupivacaine, also known as free bupivacaine. For example, the composition may comprise less than 10%, 9%, 8%, 7.5%, 7%, 6.5%, 6%, 5.5%, 5%, 4.5%, 4%, 3.5%, 3%, 2.5%, 2%, 1.5%, 1% or 0.5% by weight of unencapsulated bupivacaine. For example, the unencapsulated bupivacaine (i.e., in the aqueous supernatant of the composition) may be about 0.01 mg/mL, 0.02 mg/mL, 0.05 mg/mL, 0.1 mg/mL, 0.12 mg/mL, 0.14 mg/mL 0.16 mg/mL, 0.18 mg/mL, 0.2 mg/mL, 0.25 mg/mL, 0.3 mg/mL, 0.35 mg/mL, 0.4 mg/mL, 0.45 mg/mL, or 0.5 mg/mL. In some further embodiments, such pharmaceutical composition is for a single injection or administration (i.e., a single dose). A single administration of the composition may provide sustained release of bupivacaine for 5 to 15 days, 6 to 14 days, 8 to 14 days, or 9 to 12 days.

Lipid Components

In some embodiments of the compositions described herein, the lipid components or lipid membranes of the MVLs comprise at least one amphipathic lipid and at least one neutral lipid.

A "water-in-oil" type emulsion is formed from two immiscible phases, a lipid phase and a first aqueous phase. The lipid phase is made up of at least one amphipathic lipid and at least one neutral lipid in a volatile organic solvent, and optionally cholesterol and/or cholesterol derivatives. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids include, but are not limited to zwitterionic phospholipids, including phosphatidylcholines, phosphatidylethanolamines, sphingomyelins, lysophosphatidylcholines, and lysophosphatidylethanolamines; anionic amphipathic phospholipids such as phosphatidylglycerols, phosphatidylserines, phosphatidylinositols, phosphatidic acids, and cardiolipins; cationic amphipathic lipids such as acyl trimethylammonium propanes, diacyl dimethylammonium propanes, stearylamine, and the like. Non-limiting exemplary phosphatidyl cholines include dioleyl phosphatidyl choline (DOPC), dierucoyl phosphatidyl choline or 1,2-dierucoyl-sn-glycero-3-phosphocholine (DEPC), 1,2-didecanoyl-sn-glycero-3-phosphocholine (DDPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phoshocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC). Non-limiting examples of phosphatidyl glycerols include dipalmitoylphosphatidylglycerol or 1,2-dipalmitoyl-sn-glycero-3-phospho-rac-(1-glycerol) (DPPG), 1,2-dierucoyl-sn-glycero-3-phospho-rac-(1-glycerol) (DEPG), 1,2-dilauroyl-sn-glycero-3-phospho-rac-(1-glycerol) (DLPG), 1,2-dimyristoyl-sn-glycero-3-phospho-rac-(1-glycerol) (DMPG), 1,2-dioleoyl-sn-glycero-3-phospho-rac-(1-glycerol) (DOPG), 1,2-distearoyl-sn-glycero-3-phospho-rac-(1-glycerol) (DSPG), 1-palmitoyl-2-oleoyl-sn-glycero-3-phospho-rac-(1-glycerol) (POPG), or salts thereof, for example, the corresponding sodium salts, ammonium salts, or combinations of the salts thereof.

Suitable neutral lipids include but are not limited to triglycerides, propylene glycol esters, ethylene glycol esters, and squalene. Non-limiting exemplary triglycerides useful in the instant compositions and processes are triolein (TO), tripalmitolein, trimyristolein, trilinolein, tributyrin, tricaproin, tricaprylin (TC), and tricaprin. The fatty chains in the triglycerides useful in the present application can be all the same, or not all the same (mixed chain triglycerides), or all different. Propylene glycol esters can be mixed diesters of caprylic and capric acids.

In some further embodiments, the lipid components contain phosphatidyl choline or salts thereof, phosphatidyl glycerol or salts thereof, and at least one triglyceride. In further embodiments, the phosphatidyl choline and the phosphatidyl glycerol are present in MVLs in a mass ratio of about 10:1 to about 3:1, about 9:1 to about 3:1, or about 8:1 to about 4:1, or about 7:1 to about 5:1 or about 6:1.

In some embodiments, the amphipathic lipid comprises phosphatidylcholine, or phosphatidylglycerol or salts thereof, or combinations thereof. In some embodiments, the phosphatidyl choline is dierucoyl phosphatidyl choline (DEPC). In some embodiments, the phosphatidyl glycerol is dipalmitoyl phosphatidyl glycerol (DPPG) or a salt thereof (such as sodium DPPG). In some embodiments, the phosphatidylcholine is selected from DEPC, DSPC, DMPC, DOPC, and salts and a combination thereof. In further embodiments, the DEPC and the DPPG are present in MVLs in a mass ratio of DEPC:DPPG of about 10:1 to about 1:1, about 9:1 to about 3:1, about 8:1 to about 4:1, or about 7:1 to about 5:1 or about 6:1. In further embodiments, the mass ratio of tricaprylin to triolein is about 3:1, 4:1, 5:1, 6:1, 7:1, 8:1, 9:1, 10:1, 11:1, 12:1, 15:1, 18:1, 20:1, 22:1, or 25:1. In some embodiments, the lipid components of the bupivacaine MVLs are DEPC, DPPG or a salt thereof (such as sodium salt), cholesterol, tricaprylin and triolein. In some such embodiments, the concentration of DEPC in the composition is from about 8 mg/mL to 12 mg/mL, about 9 mg/mL to about 9.5 mg/mL, or about 8.5 mg/mL to about 10 mg/mL. In some such embodiments, the concentration of DPPG or a salt thereof in the composition is from about 0.7 mg/mL to about 1.5 mg/mL, from about 0.8 mg/mL to about 1.4 mg/mL, or about 1.1. In some such embodiments, the concentration of cholesterol in the composition is from about 4 mg/mL to about 7 mg/mL, about 4.4 mg/mL to about 6 mg/mL, or about 5.4 mg/mL to about 5.6 mg/mL. In some such embodiments, the concentration of tricaprylin in the composition is from about 2 mg/mL to about 5 mg/mL, about 2.2 mg/mL to about 4.5 mg/mL, about 2.4 mg/mL to about 2.6 mg/mL, or about 3.7 mg/mL to about 4.4 mg/mL. In some such embodiments, the concentration of triolein in the composition is about 0.3 mg/mL to about 1.0 mg/mL, about 0.7 mg/mL to about 0.9 mg/mL, about 0.8 mg/mL, or from about 0.4 mg/mL to about 0.5 mg/mL. In contrast, the Exparel® lipid components do not include triolein and the lipid concentrations are the following: DEPC (8.2 mg/mL), DPPG (0.9 mg/mL), cholesterol (4.7 mg/mL) and tricaprylin (2.0 mg/mL).

In further embodiments, the neutral lipid comprises triglyceride, propylene glycol ester, ethylene glycol ester, or squalene, or combinations thereof. In some embodiments the neutral lipid comprises triglyceride. In some embodiments the triglyceride comprises triolein or tricaprylin, or a combination thereof. In some further embodiments, the multivesicular liposomes further comprise cholesterol and/or a plant sterol.

pH Modifying Agents

In some embodiments of the bupivacaine MVL compositions described herein, the plurality of internal aqueous chambers of the MVLs may include one or more pH modifying agents. The pH modifying agents that may be used in the present MVL compositions are selected from organic acids, organic bases, inorganic acids, or inorganic bases, or combinations thereof. Suitable inorganic acids (also known as mineral acids) that can be used in the present application include, but are not limited to hydrochloric acid (HCl), sulfuric acid ($H_2SO_4$), phosphoric acid ($H_3PO_4$), nitric acid ($HNO_3$), etc. Suitable organic acids that can be used in the present application include, but are not limited to acetic acid, aspartic acid, citric acid, formic acid, glutamic acid, glucuronic acid, lactic acid, malic acid, tartaric acid, etc. Suitable organic bases that can be used in the present application include, but are not limited to histidine, arginine, lysine, tromethamine (Tris), etc. Suitable inorganic bases that can be used in the present application include, but are not limited to sodium hydroxide, calcium hydroxide, magnesium hydroxide, potassium hydroxide, etc.

In some embodiments, the pH modifying agents are selected from the group consisting of inorganic acids, organic bases, and combinations thereof. In some embodiments, the pH modifying agents are selected from the group consisting of organic acids, organic bases, and combinations thereof. In some embodiments, the inorganic acid is phosphoric acid. In some embodiments, the organic acid is selected from glucuronic acid, tartaric acid, or glutamic acid, or a combination thereof. In some embodiments, the organic base is selected from histidine, or lysine, or combinations thereof. In some further embodiments, at least one pH modifying agent resides in the first aqueous solution of the multivesicular liposomes and said pH modifying agent comprises an inorganic acid, for example, phosphoric acid. In further embodiments, at least one pH modifying agent resides in a second aqueous solution used in the process of preparing the multivesicular liposomes, and said pH modifying agent comprises an organic base. In further embodiments the organic base comprises histidine, lysine, or a combination thereof.

In some embodiments, the plurality of internal aqueous chambers of the MVLs has a pH of about 1.5, 2.0, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.2, 4.5, 4.7, 4.9, 5.0, 5.5, or 6.0, or within a range defined by any two of the preceding pH values. In some embodiments, the bupivacaine encapsulated multivesicular liposomes have an internal pH from about 2.0 to about 6.0, from about 2.5 to about 5.8, or from about 3.0 to about 5.5. In further embodiments, the internal pH of the BUP-MVLs has an internal pH from about 3.8 to about 6.0, about 4.0 to about 4.5, or about 5.0 to 5.5. The internal pH of the BUP-MVLs is important for the sustained release rate of the bupivacaine from the MVL particles.

In some embodiments of the bupivacaine MVL compositions described herein, the MVL particles are suspended in an aqueous medium. The aqueous medium may comprise one or more pH modifying agents, and/or may perform a buffering function. The aqueous medium defines the external pH of the MVL composition. In some embodiments, the pH of the aqueous medium is about 3.5, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.7, 7.0, 7.5, 8.0, 8.5, or 9.0, or within a range defined by any two of the preceding pH values. In some embodiments, the bupivacaine encapsulated multivesicular liposomes have an external pH (i.e., the pH of the suspending solution where multivesicular liposome particles reside) from about 3.0 to about 7.5. In some further embodiments, the external pH is from about 4.0 to about 7.0, or from about 4.5 to about 6.5. In some other embodiments, the pH of the aqueous medium is from about 6.0 to about 7.5 or from about 6.5 to about 7.5. In some embodiments, the pH of the aqueous medium is about 7.0. In some embodiments, the buffering agent includes sodium phosphate. As such, the bupivacaine MVL particles are suspended in a sodium phosphate buffered saline solution. The concentration of sodium phosphate present in the water-immiscible solvent used to make the MVLs typically range from 1-50 mM, 2-40 mM, or 5-20 mM. In some embodiments, the concentrations of the sodium phosphate in the composition is about 10 mM.

Tonicity Agents

In some embodiments of the bupivacaine MVL compositions described herein, the first and or the second aqueous solution of the MVLs further comprises one or more tonicity agents. Tonicity agents sometimes are also called osmotic agents. Non-limiting exemplary osmotic agents suitable for the MVL composition of the present application include monosaccharides (e.g., glucose, and the like), disaccharides (e.g., sucrose and the like), polysaccharide or polyols (e.g., sorbitol, mannitol, Dextran, and the like), or amino acids.

In some embodiments, the one or more tonicity agents may be selected from an amino acid, a sugar, or combinations thereof. In some further embodiments, one or more tonicity agents are selected from dextrose, sorbitol, sucrose, lysine, or combinations thereof.

In some embodiments, the osmolality of the aqueous medium is from about 280 mOsm/kg to about 500 mOsm/kg, about 280 mOsm/kg to about 360 mOsm/kg, or about 330 mOsm/kg.

Particle Sizes

In some embodiments of the bupivacaine MVL compositions described herein, the bupivacaine encapsulated MVL particles have a median particle diameter of about 5, 10, 15, 20, 25, 30, 35, 40, 45, 50, 55, 60, 65, 70, 75, 80, 85, 90, 95, or 100 μm, or within a range defined by any two of the preceding values. In some further embodiments, the multivesicular liposomes have a median particle diameter ($D_{50}$) ranging from about 7 μm to about 40 μm. In some further embodiments, the multivesicular liposomes have a median particle diameter ranging from about 10 μm to about 35 μm, or 15 μm to about 30 μm. In still some further embodiments, the multivesicular liposomes have a median particle diameter ($D_{50}$) ranging from about 20 μm to about 30 μm.

In some embodiments of the bupivacaine MVL compositions described herein, the bupivacaine encapsulated MVL particles have an average $D_{90}$ particle diameter of about 30, 35, 40, 45, 50, 55, 60, 65, 70, 75, 80, 85, or 90 μm, or within a range defined by any two of the preceding values. In some further embodiments, the multivesicular liposomes have an $D_{90}$ particle diameter ranging from about 30 μm to about 90 μm. In some further embodiments, the multivesicular liposomes have an average $D_{90}$ particle diameter ranging from about 30 μm to about 80 μm, or 35 μm to about 70 μm. In some further embodiments, the MVL particles have particle size span ($D_{10}$-$D_{90}$) of about 30 m, 35 μm, 40 μm, 45 μm, 50 μm, 55 μm, 60 μm, 65 μm, 70 μm, or 75 μm.

In some embodiments, the MVLs may optionally comprise additional therapeutic agent(s). In some other embodiments, bupivacaine is the only therapeutic agent in the MVLs.

In some embodiments, the MVL particles are suspended in a liquid suspending solution or medium (e.g., aqueous medium) to form an MVL composition. In some further embodiments, the liquid suspending medium is a buffered saline solution. In some such embodiments, the MVL particle suspension has a PPV (%) of about 30%, 35%, 40%, 45%, 50%, 55%, 60%, 65%, 70%, 75% or 80%. In further embodiments, the concentration of bupivacaine in the MVL composition is about 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 32 mg/mL, 34 mg/mL, 36 mg/mL, 38 mg/mL or 40 mg/mL, or in a range defined by any of the two preceding values. In some further embodiments, the concentration of bupivacaine in the MVL composition is from about 18 mg/mL to about 40 mg/mL, from about 20 mg/mL to about 30 mg/mL, from about 22 mg/mL to about 28 mg/mL, or from about 24 mg/mL to about 26 mg/mL, from about 18 mg/mL to about 24 mg/mL, or from about 18 mg/mL to about 22 mg/mL.

In any embodiments of the bupivacaine multivesicular liposome compositions described herein, the multivesicular liposomes are stable at 25° C., 30° C., or 37° C. for at least 2, 3, 4, 5, 6, or 7 days. Furthermore, the composition may be stable at 5° C. for at least 1 week, 2 weeks, 3 weeks, 4 weeks, 2 months, 3 months, 6 months, 9 months, 12 months, 18 months or 24 months. As used herein, the term "stable" means that the multivesicular liposomes particles in the suspending solution maintain the structural integrity and bupivacaine remains encapsulated in the multivesicular liposomes without excessively leaking out of multivesicular liposomes in free form, during certain storage condition for a period of time. In some embodiments, the BUP-MVL compositions described herein are stable at 5° C. for 6 months with less than about 10%, 9%, 8%, 7%, 6%, 5%, 4%, 3%, 2%, 1%, 0.5%, or 0.1% of bupivacaine by weight in the free or unencapsulated form. In some embodiments, the BUP-MVL compositions described herein are stable at 25° C., 30° C. or 37° C. for 3 days with less than about 30%, 25%, 20%, 15%, 10%, 9%, 8%, 7%, 6%, 5%, 4%, 3%, 2%, or 1% of bupivacaine by weight in the free or unencapsulated form. In some embodiments of the composition described herein, the increase of unencapsulated bupivacaine in the composition is less than about 20%, 19%, 18%, 17%, 16%, 15%, 14%, 13%, 12%, 11%, 10%, 9%, 8%, 7%, 6%, 5%, 4%, 3%, 2%, 1% by weight after the composition is stored at 5° C. for six months. For example, in some embodiments, the free bupivacaine may be about 4% or less by weight when stored at 25° C. for 3 months. In other embodiments, the free bupivacaine may be about 2% or less by weight when stored at 5° C. for 6 months.

In any embodiments of the bupivacaine multivesicular liposome compositions described herein, bupivacaine is in a salt form. In some embodiment, bupivacaine is in the form of bupivacaine phosphate.

Methods of Manufacturing

Some embodiments of the present application relate to a process for preparing bupivacaine encapsulated multivesicular liposomes, the process comprising: mixing a first aqueous solution with a lipid solution comprising at least one organic solvent, at least one amphipathic lipid, and at least one neutral lipid to form a first water-in-oil emulsion, wherein at least one of the first aqueous solution and the lipid solution comprises bupivacaine; combining the first water-in-oil emulsion with a second aqueous solution to form a second emulsion; substantially removing the organic solvent from the second emulsion to form a first aqueous suspension of bupivacaine encapsulated MVLs; and exchanging the aqueous supernatant of the first aqueous suspension with a third aqueous solution one or more times to provide a final aqueous suspension of bupivacaine encapsulated MVLs. In some embodiments, the bupivacaine concentration in the final aqueous suspension is at least about 18 mg/mL, for example, from about 18 mg/mL to about 40 mg/mL. In further embodiments, the bupivacaine concentration in the final aqueous suspension is about 18 mg/mL to about 24 mg/mL, about 18 mg/mL to about 22 mg/mL, or about 20 mg/mL.

In some embodiments of the process described herein, the organic solvent is substantially removed by exposing the second emulsion to a gas atmosphere. Organic solvent may be removed by blowing a gas over the second emulsion, or sparging gas in the second emulsion, or spraying the second emulsion into a chamber with a continuous stream of circulating gas.

In any embodiments of the process described herein, the first aqueous solution comprises at least one pH modifying agent. In some embodiments, the pH modifying agent of the first aqueous solution is an inorganic acid, an organic acid, an inorganic base, or an organic base, or combinations thereof. In some such embodiments, the pH modifying agent is phosphoric acid. In some embodiments, the first aqueous solution may also include one or more osmotic agents. The osmotic agent may be selected from a saccharide, such as sucrose. In some such embodiments, the volume of the lipid solution is greater than the volume of the first aqueous solution. In some other embodiments of the process described herein, bupivacaine is incorporated into the lipid solution. In some such embodiments, the volume of the lipid solution is the same or substantially the same as the volume of the first aqueous solution, for example, the volume of the lipid solution and the volume of the first aqueous solution is about 1:1.

In some embodiments of the process described herein, the pH range of the first aqueous solution is about 0.8, 0.9, 1.0, 1.1, 1.2, 1.3, 1.4, 1.5, 1.6, 1.7, 1.8, 1.9, 2.0 or 2.5, or a range defined by any two of proceeding values. In some further embodiments, the pH range of the first aqueous solution is from about 1.0 to about 1.5, or from about 0.8 to about 2.5. In certain cases, it was observed that when the pH level was high in the first aqueous solution, the encapsulated bupivacaine was more likely to leak out of the MVLs. A mildly acidic internal pH environment of the MVLs is beneficial to the encapsulation efficiency of the bupivacaine, and further contributes to the improved pharmacokinetic profiles of the BUP-MVLs for extended period of time. However, a pH level that is too low in the first aqueous solution renders the MVL particles less stable due to increased lipid membrane hydrolysis.

As described herein, the internal pH of the final BUP-MVLs is important for the sustained release profile of the bupivacaine. During the manufacturing process, the internal pH of the final product may be controlled by the pH of first aqueous solution, where bupivacaine is mixed with one or more pH adjusting agents. In some embodiments, the molar ratio of bupivacaine to the pH adjusting agent(s) (e.g., organic and/or inorganic acids) in the first aqueous solution is from about 1:1.2 to about 1:4. In some further embodiments, the molar ratio of the bupivacaine and the pH adjusting agent(s) in the first aqueous solution is about 1:1, 1:1.1, 1:1.2, 1:1.3, 1:1.4, 1:1.5, 1:1.6, 1:1.7, 1:1.8, 1:1.9, 1:2, 1:2.5, 1:3 or 1:3.5. In further embodiments, the ratio of bupivacaine to the pH adjustment agent(s) is between about 1:1.4 to 1:2. In some further embodiments, the bupivacaine loading solution is about 40-75 mg/mL or about 60 mg/mL in the lipid solution (about 140-320 mM). In one embodiment, the pH adjusting or modifying agent comprises or is an inorganic acid (e.g., phosphoric acid).

In some embodiments of the process described herein, the osmolality of the first aqueous solution of the MVLs is about 200, 220, 230, 235, 240, 245, 250, 250, 260, 265, 270, 275, 280, 285, 290, 295, 300, 305, 310, 315, 320, 325, 330, 335, 340, 350, 360, 370, 380, 390, 400, 410, 420, 430, 440, 450, 460, 470, 480, 490, 500, 510, 520 or 550 mOsm/kg, or within a range defined by any two of the preceding values. In some further embodiments, the osmolality of the first aqueous solution of the MVLs is from about 240 mOsm/kg to about 520 mOsm/kg, 250 mOsm/kg to about 480 mOsm/kg, 200 mOsm/kg to about 300 mOsm/kg, or from about 300 mOsm/kg to 500 mOsm/kg.

In some embodiments of the process described herein, the second aqueous solution comprises at least one pH modifying agent and at least one tonicity agent. In some such embodiments, the tonicity agent comprises sorbitol, sucrose, or dextrose, or combinations thereof. In some such embodiments, the pH modifying agent comprises lysine or histidine, or combinations thereof. In some embodiments, the osmolality of the second aqueous solution is about 200, 205, 210, 215, 220, 225, 230, 235, 240, 245, 250, 255, 260, 265, 270, 275, 280, 285, or 290 mOsm/kg, or in a range defined by any two of the preceding values. In some embodiments, the osmolality of the second aqueous solution is from about from about 200 mOsm/kg to about 290 mOsm/kg, from about 205 mOsm/kg to about 285 mOsm/kg, or from about 210 mOsm/kg to about 270 mOsm/kg. It is important to keep the osmolality of the the second aqueous solution to be hypotonic to reduce MVL particle aggregations and also provide a more uniform MVL particle size distribution.

In some embodiments of the process described herein, the pH range of the second aqueous solution is about 5.0, 5.5, 6.0, 6.5, 7.0, 7.5, 8.0, 8.5, 9.0, 9.5, 10, 10.5, 11, 11.5, or 12 or in a range defined by any two of the preceding values. In some such embodiments, the pH range of the second aqueous solution is about 6.0 to about 11.5, about 7.0 to about 11, or about 9 to about 10.

After the organic solvent is removed, the resulting multivesicular liposome particles are diluted, centrifuged and/or filtered (e.g., by microfiltration or tangential flow filtration (TFF)), and the supernatant is replaced with a third aqueous solution, where the third aqueous solution comprise saline, optionally containing one or more buffering agents (e.g., 20 mM sodium phosphate at pH from 5.5 to 7.6, for example at pH 6.8 or 7). After washing, the MVL particles were diluted in saline or other buffer solutions to yield the final product as a composition comprising an aqueous medium in which the bupivacaine encapsulated MVLs are suspended with about 35% or about 80%, from 40% to about 65%, or from 45% to about 55% packed particle volume (PPV). In some such embodiments, the concentration of encapsulated bupivacaine in the suspension is from about 18 mg/mL to about 40 mg/mL, from about 18 mg/mL to about 24 mg/mL, or from about 18 mg/mL to about 22 mg/mL, or about 20 mg/mL. In some such embodiments, the unencapsulated or free bupivacaine is about 10%, 9%, 8%, 7%, 6%, 5%, 4%, 3%, 2%, 1%, 0.9%, 0.8%, 0.7%, 0.6%, 0.5%, 0.4%, 0.3%, or 0.2% or less by weight of total amount of bupivacaine in the suspension. In some embodiments, the concentration of unencapsulated bupivacaine in the final product suspension is less than about 4 mg/mL, 3.5 mg/mL, 3 mg/mL, 2.5 mg/mL, 2.0 mg/mL, 1.5 mg/mL, 1 mg/mL, 0.9 mg/mL, 0.8 mg/mL, 0.7 mg/mL, 0.6 mg/mL, 0.5 mg/mL, 0.4 mg/mL, 0.3 mg/mL, 0.2 mg/mL, 0.1 mg/mL, 0.05 mg/mL or 0.01 mg/mL.

In some embodiments, the osmolality of the aqueous medium after the MVLs are formed is about 250, 260, 270, 280, 290, 300, 310, 320, 330, 340, 360, 380, 400, 420, 440, 460, 480, or 500 mOsm/kg, or in a range defined by any two of the preceding values. In some embodiments, the osmolality of the aqueous medium is from about 280 mOsm/kg to about 360 mOsm/kg. In some embodiments, the initial osmolality of the aqueous medium after the MVLs are formed is about 330 mOsm/kg.

In some embodiments, the process further includes adjusting the osmolality of the aqueous suspension of bupivacaine encapsulated MVLs after the MVLs are formed. In some embodiments, the initial osmolality of the first aqueous solution is from about 200 mOsm/kg to about 500 mOsm/kg and the process further comprises increasing the osmolality of the aqueous suspension of bupivacaine encapsulated MVLs after MVLs are formed. In some embodiments, the osmolality of the aqueous suspension is increased by adding one or more tonicity agents to the aqueous suspension or by resuspending the bupivacaine MVLs in a suspending solution with higher osmolality. In some embodiments, the initial osmolality of the first aqueous solution is from about 350 mOsm/kg to about 500 mOsm/kg, and the process further comprises decreasing the osmolality of the aqueous suspension of bupivacaine encapsulated MVLs after MVLs are formed. In some embodiments, the osmolality of the aqueous suspension is decreased by adding water or resuspending the MVLs in a suspending solution with lower osmolality than the initial aqueous suspension of MVLs. In some embodiments, the osmolality of the aqueous suspension of bupivacaine encapsulated multivesicular liposomes is adjusted to, or to about, 250, 260, 270, 280, 290, 300, 310, 320, 330, 340, 350, or 360 mOsm/kg, or in a range defined by any two of the preceding values, after the MVLs are formed.

Some further embodiments of the present disclosure include bupivacaine encapsulated multivesicular liposomes prepared by the process described herein.

In some embodiments of the process described herein, the lipid solution contains phosphatidyl choline or salts thereof, phosphatidyl glycerol or salts thereof, and at least one triglyceride. In some embodiments, the amphipathic lipid comprises phosphatidylcholine, or phosphatidylglycerol or salts thereof, or combinations thereof. In some embodiments, the phosphatidyl choline is dierucoyl phosphatidyl choline (DEPC). In some embodiments, the phosphatidyl glycerol is dipalmitoyl phosphatidyl glycerol (DPPG) or a salt thereof (e.g., a sodium salt). In some embodiments, the phosphatidylcholine is selected from DEPC, DSPC, DMPC, DOPC, or a combination thereof. In further embodiments, the neutral lipid comprises triglyceride, propylene glycol ester, ethylene glycol ester, or squalene, or combinations thereof. In some embodiments the neutral lipid comprises triglyceride. In some embodiments the triglyceride comprises triolein or tricaprylin, or a combination thereof. In some further embodiments, the multivesicular liposomes further comprise cholesterol and/or a plant sterol.

The concentrations of the amphipathic lipids, neutral lipids, and cholesterol present in the water-immiscible solvent used to make the MVLs typically range from 1-120 mM, 2-120 mM, and 10-120 mM, respectively. In some embodiments, the concentrations of the amphipathic lipids, neutral lipids, and cholesterol may range from about 20 mM to about 60 mM, about 8 mM to about 60 mM, and about 20 to about 60 mM, respectively. In some embodiments, the lipid components of the lipid solution include DEPC, DPPG (or sodium DPPG), cholesterol, tricaprylin and triolein. For example, the concentration of DEPC in the lipid solution may be from about 15 mM to about 40 mM, from about 20 mM to about 35 mM, or about 30 mM. The concentration of DPPG (or sodium DPPG) in the lipid solution may be from about 3.5 mM to about 14 mM, from about 4 mM to about 10 mM, or about 5.2 mM. The concentration of tricaprylin in the lipid solution may be from about 8 mM to about 50 mM, from about 9 mM to about 25 mM, or about 10 mM to about 15 mM. The concentration of triolein in the lipid solution is from about 0.5 mM to about 5 mM, from about 1 mM to about 3 mM, or from about 1.5 mM to about 2.5 mM. The concentration of cholesterol in the lipid solution may be from about 25 mM to about 60 mM, from about 35 mM to about 50 mM or about 40 mM. In contrast, the Exparel® product with 13.3 mg/mL bupivacaine concentration does not include triolein in the lipid components. The lipid components in the starting lipid solution are about 20 mM DEPC, 3.5 mM DPPG (Na), 26.7 mM cholesterol, and 9.2 mM tricaprylin.

In some embodiments, adjusting the concentration of certain lipid component(s) may have an impact on the sustained release rate of bupivacaine. While it is generally understood that when a higher concentration of the lipid component(s) is used in the manufacturing process of the MVLs, a slower release of the active agent may be observed, at least partially due to the improved strength of the lipid membrane of the MVL particles. However, high lipid concentrations may also have certain drawbacks, such as difficulty in handling of the lipid mixture due to increased stickiness and clogging of the pores of the filter during the filtration of the MVL particles. In some embodiments, the BUP-MVLs comprise DPPG in the lipid membranes. In some instances, decreasing the amount of DPPG in the lipid solution during the process described herein may lead to improvement in aggregation of the MVL particles. Surprisingly, it has been observed that reducing the amount of DPPG the lipid combo did not affect the PK profile relative to the batches made with higher amount of DPPG. In some such embodiments, the concentrations of the amphipathic lipids (such as phosphotidylcholine or phosphotidylglycerol or salts thereof) in the water-immiscible solvent used to make the MVLs range from about 3 mM to about 55 mM, from about 3 mM to about 15 mM, or from about 18 mM to about 40 mM. In further embodiments, the concentrations of DPPG in the water-immiscible solvent used to make the MVLs range from about 3 mM to about 17 mM, from about 5 mM to about 12.5 mM, or from about 8 mM to about 10 mM.

Many types of volatile organic solvents can be used in the present application, including ethers, esters, halogenated ethers, hydrocarbons, halohydrocarbons, or freon. For example, diethyl ether, chloroform, methylene chloride, tetrahydrofuran, ethyl acetate, and any combinations thereof are suitable for use in making the compositions. In some embodiments, methylene chloride is used. In some other embodiments, chloroform is used.

The lipid solution and first aqueous solution are mixed by mechanical turbulence, such as through use of rotating or vibrating blades, shaking, extrusion through baffled structures or porous pipes, or by ultrasound, or by the use of a three fluid nozzle (described in U.S. Pat. No. 9,737,482) to produce a water-in-oil emulsion. The water-in-oil emulsion can then be dispersed into a second aqueous solution by means described above, to form solvent-containing spherules suspended in the second aqueous solution, a water-in-oil-in-water emulsion is formed. The term "solvent-containing spherules" refers to a microscopic spheroid droplet containing organic solvent, within which are suspended multiple smaller droplets of aqueous solution.

The volatile organic solvent is then removed from the spherules by exposing to a pressurized stream of gas. For instance, such a pressurized stream of gas can cause surface evaporation from the second emulsion, sparging the second emulsion with a gas, or contacting the second emulsion with a gas in a spray chamber. When the solvent is substantially or completely evaporated, MVLs are formed. In some embodiments, the process further includes diluting the second emulsion in a third aqueous solution prior to substantially removing the organic solvent. In some embodiments, the third aqueous solution may be the same or substantially the same as the second aqueous solution. Gases which can be used for the evaporation include nitrogen, argon, helium, oxygen, hydrogen, and carbon dioxide, mixtures thereof, or clean compressed air. Alternately, the volatile solvent can be removed by sparging, rotary evaporation, diafiltration or with the use of solvent selective membranes, or contacting with a gas in a spray chamber.

As discussed above, bupivacaine can be incorporated in the MVL by inclusion in the first aqueous solution. bupivacaine can also be incorporated in the MVLs by inclusion in the lipid solution or both the lipid and first aqueous solution. The amount of bupivacaine recovered in the MVLs was assayed by diluting the suspension of the BUP-MVL 50 fold into 100% methanol, then injecting the resulting mixture into an HPLC (Hewlett-Packard Model 1100 with C-18 column; running solvent system: 51% MeOH; 49% aqueous buffer containing monobasic sodium phosphate ($NaH_2PO_4$), $H_3PO_4$, TEA and sodium dodecyl sulfate ("SDS"); pH=2.5) as described in the United States Pharmacopeia 37 (USP 37) assay for organic impurities with some minor modification. In some embodiments, the percent bupivacaine yield is from about 40% to about 90% of the starting bupivacaine amount, more preferably from about 50% to about 90%, more preferably from about 60% to about 90%.

Standard preparation of multivesicular liposomes is illustrated in U.S. Pat. Nos. 5,766,627 and 6,132,766, each of which is incorporated by reference in its entirety. Alternatively, bupivacaine can be remotely loaded to the blank MVL particles, which is described in U.S. Pat. No. 9,974,744.

In any embodiments of process described herein, bupivacaine may be in a salt form. In some embodiment, bupivacaine is in the form of bupivacaine phosphate.

In any embodiments of the process described herein, all the steps of the process is carried out in an aseptic conditions and the final BUP-MVLs may be directly used for pharmaceutical administration without further purification.

Methods of Treatment and Administration

Some embodiments of the present application are related to methods for treating or ameliorating pain, comprising administering a BUP-MVL composition, as described herein, to a subject in need thereof. For example, the instant BUP-MVL compositions can be used for pre-surgical medication or post-surgical pain (e.g., spinal surgery, pain associated with cesarean section surgery, bunionectomy, total knee arthroplasty, or oral and maxillofacial procedures). In some embodiment, the pain is chronic pain. In some embodiments, the chronic pain is myofascial pain syndromes, complex regional pain syndromes, or radicular back pain.

In some embodiments, the administration is via local infiltration to a surgical site. In some embodiments, the administration is via a nerve block. For example, the administration is via interscalene brachial plexus nerve block, femoral nerve bloc, sciatic nerve block, or ganglion block. In some embodiments, the method is for treating post-surgical pain. For example, pain associated with cesarean section surgery, bunionectomy, total knee arthroplasty, or oral and maxillofacial procedures.

In some embodiments of the methods described herein, the administration is parenteral. In some further embodiments, the parenteral administration may be selected from the group consisting of infiltration, subcutaneous injection, tissue injection, intramuscular injection, intraarticular, spinal injection, intraocular injection, epidural injection, subarachnoid injection, sacroiliac joints injection, intrathecal injection, caudal injection, intraotic injection, perineural injection, and combinations thereof. In particular embodiments, the parenteral administration is subcutaneous injection or tissue injection. In some further embodiments, the instant compositions can be administered by bolus injection, e.g., subcutaneous bolus injection, intramuscular bolus injection, intradermal bolus injection and the like. In one embodiment, the administration is via local infiltration to a surgical site to provide local analgesia. In some embodiments, the administration is via a nerve block to provide regional analgesia. In one example, the administration is via interscalene brachial plexus nerve block. In another example, the administration is via femoral nerve block (e.g., in the adductor canal for postsurgical regional analgesia in patients undergoing total knee arthroplasty). In another example, the administration is via ganglion block. In another example, the administration is via sciatic nerve block (e.g., in the popliteal fossa for postsurgical regional analgesia in patients undergoing bunionectomy).

Administration of the bupivacaine MVL composition may be accomplished using standard methods and devices, e.g., pens, injector systems, needle and syringe, a subcutaneous injection port delivery system, catheters, and the like. The administration of the bupivacaine MVLs composition may be used in conjunction with Pacira's handheld cryoanalgesia device. In some embodiment, the administration may be via injection of a single dose of the BUP-MVL product (e.g., 5 mL, 10 mL, 15 mL or 20 mL).

In some embodiments, the BUP-MVL composition may be administered every 5, 6, 7, 8, 9, 10, 11, 12, 13, 14, 15, 16, 17, 18, 19, 20 or 21 days. In some such embodiments, the composition may be administered every 8 to 14 days, or about every 9 to 13 days. The number of administrations may change depending on effectiveness of the dose, observed side effects, desire to titrate up to a desired dose, external factors (e.g., a change in another medication), or the length of time that the dosage form has been administered. In some embodiments, the $T_{max}$ of bupivacaine of the administered BUP-MVL composition is, or is about, 6 hours, 12 hours, 18 hours, 24 hours, 30 hours, 36 hours, 42 hours, 48 hours, 54 hours, 60 hours, 66 hours, 72 hours, 78 hours, 84 hours, 90 hours, 96 hours, 102 hours, 108 hour, 114 hours, or 120 hours, or any range of values therebetween. In some embodiments, the percent AUC or cumulative AUC (0-24 hours) of bupivacaine of the administered BUP-MVL composition is, or is about, 1%, 2%, 3%, 4%, 6%, 8%, 10%, 12%, 15%, 20%, or 25%, or any range of values therebetween. For example, from about 6% to about 20%, or from about 8% to about 15%. In some embodiments, the total percent AUC is above 90% from 96 hours, 102 hours, 108 hours, 114 hours, 120 hours, 126 hours, 132 hours, 138 hours, 144 hours, 150 hours, 156 hours, 162 hours, 168 hours, 174 hours, 180 hours, 186 hours, 192 hours, 198 hours, 204 hours, 210 hours, 216 hours, 220 hours, 240 hours, 260 hours, 280 hours or 300 hours post administration. For example, in some embodiments, the total percent AUC is above 90% from 192 hours to about 216 hours post administration.

In some embodiments, the BUP-MVL composition comprises free or unencapsulated bupivacaine, at less than about 10%, 9%, 8%, 7.5%, 7%, 6.5%, 6%, 5.5%, 5%, 4.5%, 4%, 3.5%, 3%, 2.5%, 2%, 1.5%, 1%, 0.9%, 0.8%, 0.7%, 0.6%, 0.5%, 0.4%, 0.3%, or 0.2% by weight of unencapsulated bupivacaine. In some embodiments, the BUP-MVL composition comprises free or unencapsulated bupivacaine, at less than 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2 mg/mL, 2.2 mg/mL, 2.4 mg/mL, 2.6 mg/mL, 2.8 mg/mL, 3 mg/mL or 4 mg/mL of unencapsulated bupivacaine. In further embodiments, a single dose of bupivacaine MVL composition described herein is administered every 5-14 days or every 7 days.

Pharmaceutical Compositions

In some embodiments, the composition comprising bupivacaine MVLs is a pharmaceutical composition includes a pharmaceutically acceptable carrier. Effective injectable bupivacaine MVLs compositions is in a liquid suspension form. Such injectable suspension compositions require a liquid suspending medium (e.g., aqueous medium), with or without adjuvants, as a vehicle. The suspending medium can be, for example, aqueous solutions of sodium chloride (i.e., saline solution), dextrose, sucrose, polyvinylpyrrolidone, polyethylene glycol, a pH modifying agent described herein, or combinations of the above. In some embodiments, the suspending medium of bupivacaine MVLs is a saline solution, optionally contain a tonicity agent such as dextrose and/or a pH modifying agent such as lysine.

Suitable physiologically acceptable storage solution components are used to keep the compound suspended in suspension compositions. The storage solution components can be chosen from thickeners such as carboxymethylcellulose, polyvinylpyrrolidone, gelatin and the alginates. Many surfactants are also useful as suspending agents. The suspending medium could also contain lecithin, alkylphenol polyethylene oxide adducts, naphthalenesulfonates, alkylbenzenesulfonates, or the polyoxyethylene sorbitan esters. In some embodiments, the bupivacaine MVL composition is free or substantially free of any additive of preservatives.

In any embodiments of the composition of bupivacaine encapsulated MVLs described herein, the composition may be a pharmaceutical composition suitable for human administration. In further embodiments, the composition may be an aqueous suspension of bupivacaine encapsulated MVL particles.

EXAMPLES

The following examples, including experiments and results achieved, are provided for illustrative purposes only and are not to be construed as limiting the present application.

Example 1: Preparation of Bupivacaine MVL Composition with Osmolality Adjustment Bupivacaine MVL compositions were manufactured as follows: Bupivacaine was solubilized in a lipid solution containing DEPC, DPPG, tricaprylin and cholesterol dissolved in dichloromethane (DCM). The lipid solution was mixed with a first aqueous solution containing phosphoric acid to form a water-in-oil (W/O) emulsion. The W/O emulsion was then mixed with a second aqueous solution at about 270 mOsm/kg containing one or more pH adjusting agent (e.g., lysine or histidine) and one or more tonicity agents (e.g., sorbitol or dextrose) to produce a water-in-oil-in-water (W/O/W) emulsion. The W/O/W emulsion was then diluted with a second aqueous solution. DCM was removed via evaporation. The resulting particles were then centrifuged and/or filtered by tangential flow filtration, and the supernatant was replaced with saline+/−buffering agents (e.g., 10 mM sodium phosphate at pH's 6.5-7.5). to yield a product with about 45-55% packed particle volume and an osmolality of about 350 mOsm/kg at a bupivacaine concentration of about 20 mg/ml.

Exemplary manufacturing conditions are summarized in Table 1 herein. Table 1 summarizes the lipid components used for various formulations. Formulations 6, 8, and 10 were made in 4 L scale.

The following abbreviations are used herein:
Chol is Cholesterol;
TC is tricaprylin;
TO is triolein;
Osmolality is mOsm/kg;
"Lipid Combo 1" is comprised of DEPC (1,2-dierucoyl-sn-glycero-3-phosphocholine, (29.7 mM, 26.67 mg/mL); DPPG (Na) (1,2-dipalmitoyl-sn-glycero-3-phospho-rac-(1-glycerol), (5.2 mM, 3.89 mg/mL); cholesterol (39.8 mM, 15.4 mg/mL); TC (tricaprylin, 24.1 mM, 11.33 mg/mL); TO (triolein, 1.4 mM, 1.21 mg/mL); and water (0.29%); the final product lipid measurement for Lipid Combo 1 was DEPC (8.4-9.97 mg/mL), DPPG (Na) (0.8-1.3 mg/mL), cholesterol (4.4-6.0 mg/mL), tricaprylin (3.7-4.4 mg/mL), and triolein (0.38-0.47 mg/mL);

"Lipid Combo 2" is comprised of DEPC (1,2-dierucoyl-sn-glycero-3-phosphocholine, (29.7 mM, 26.67 mg/mL); DPPG (Na) (1,2-dipalmitoyl-sn-glycero-3-phospho-rac-(1-glycerol), (5.2 mM, 3.89 mg/mL); cholesterol (39.8 mM, 15.4 mg/mL); TC (tricaprylin, 15.1 mM, 7.1 mg/mL); TO (triolein, 2.6 mM, 2.3 mg/mL); and water (0.29%); the final product lipid measurement for Lipid Combo 2 was DEPC (9.1-9.4 mg/mL), DPPG (Na) (1.1 mg/mL), cholesterol (5.4-5.6 mg/mL), tricaprylin (2.4-2.6 mg/mL), and triolein (0.78-0.82 mg/mL);

"EXP" is comprised of DEPC (1,2-dierucoyl-sn-glycero-3-phosphocholine, (19.8 mM, 17.8 mg/mL); DPPG (1,2-dipalmitoyl-sn-glycero-3-phospho-rac-(1-glycerol), (3.5 mM, 2.6 mg/mL); cholesterol (26.72 mM, 10.34 mg/mL); TC (tricaprylin, 9.2 mM, 4.3 mg/mL); and water (0.07%); the final product lipid measurement for EXP was DEPC (6.41-7.24 mg/mL), DPPG (Na) (0.85-0.93 mg/mL), cholesterol (4.03-4.38 mg/mL), and tricaprylin (1.54-1.63 mg/mL);

Total BUP concentration refers to the total amount of encapsulated bupivacaine in the composition, including encapsulated bupivacaine in the multivesicular liposomes and the unencapsulated bupivacaine in the aqueous suspending medium;

Percent BUP Yield refers to the amount of bupivacaine obtained in the final product particle suspension, as compared to the amount added into either the first aqueous or lipid solutions;

% PPV means packed particle volumes, measured by spinning the suspensions down with a centrifuge and measuring the height of the particles in a lipocrit tube with a ruler;

% Free means the amount of unencapsulated bupivacaine in the supernatant versus the total amount of bupivacaine in the suspension.

TABLE 1

Summary of Lipid Components

| Formulation # | Base Lipid Solution | [DEPC] (mM) | [DPPG] (mM) | [Chol] (mM) | [TC] (mM) | [TO] (mM) | Solvent |
|---|---|---|---|---|---|---|---|
| 6 | Lipid Combo 1 | 29.7 | 5.2 | 39.8 | 24.1 | 1.4 | DCM |
| 10 | Lipid Combo 2 | 29.7 | 5.2 | 39.8 | 15.1 | 2.6 | DCM |
| 8 | Lipid Combo 1 | 29.7 | 5.2 | 39.8 | 24.1 | 1.4 | DCM |

Example 2: Preparation of Bupivacaine MVL Composition Using Optimized Processing Solutions Bupivacaine MVL compositions were manufactured as follows: Bupivacaine was solubilized in a lipid solution containing DEPC, DPPG, tricaprylin and cholesterol dissolved in dichloromethane (DCM). The lipid solution was mixed with a first aqueous solution containing phosphoric acid to form a water-in-oil (W/O) emulsion. The W/O emulsion was then mixed with a second aqueous solution with a reduced osmolality of about 220 mOsm/kg, compared with Example 1, containing one or more pH adjusting agent (e.g., lysine or histidine) and one or more tonicity agents (e.g., sorbitol or dextrose) to produce a water-in-oil-in-water (W/O/W) emulsion. The W/O/W emulsion was then diluted with the second aqueous solution containing lysine or histidine and sorbitol or dextrose. DCM was removed via evaporation. The resulting MVL particles were then centrifuged and/or filtered by tangential flow filtration, and the supernatant was replaced with saline+/−buffering agents (e.g., 10 mM sodium phosphate at pH's 6.5-7.5) to yield a product with about 45-55% packed particle volume and an osmolality of about 330 mOsm/kg at a bupivacaine concentration of about 20 mg/ml. Surprisingly, the change in the second and third aqueous solution osmolality resulted in a desirable reduction in final product particle size and aggregation.

Example 3—Pharmacokinetic Studies Compositions in Rats

Pharmacokinetic studies of the subcutaneous dosing of the bupivacaine PK studies discussed herein were performed in rats where bolus bupivacaine was compared to various compositions of bupivacaine MVLs. Formulations 6, 8, and 10 had an initial % PPV of about 47%-59% and were not diluted prior to injection. The BUP concentration in the final product was approximately 20 mg/mL. Female Sprague Dawley rats were supplied by Absorption Systems weighing about 310 g and received subcutaneous injections of either a bolus of unencapsulated (free or unencapsulated) bupivacaine, or one the of the bupivacaine MVL compositions of Example 1 (with encapsulated bupivacaine in the MVLs of about 20-26 mg/mL) or Example 2 (with encapsulated bupivacaine in the MVLs of about 19-23.5 mg/mL) at doses ranging from about 30-40 mg/kg.

Plasma samples were collected at different times points (1, 2, 6, 12, 24, 48, 72, 96, 120, 144 and 168, 192, and 216-hour post dose) for analysis. Blood samples were collected via the jugular vein or other suitable blood vessel using a 19-gauge needle prick or cardiac puncture for the final time point, placed into chilled tubes containing the appropriate anticoagulant, inverted several times to mix, protected from light, and kept on ice until centrifugation. A summary of the data in FIG. 1 is set forth below in Tables 2-3.

FIG. 1 is a line chart illustrating the dose normalized bupivacaine plasma levels as a function of time, following administration of several bupivacaine encapsulated multivesicular liposomes (BUP-MVLs) compositions (Formulations 6, 8, and 10) with varying triolein concentrations and osmolarities.

TABLE 2

Summary of Select BUP-MVL Formulations

| Formulation | Total [BUP] (mg/mL) | % BUP Yield | % PPV | % Free | Ext. pH | Int. pH | PSD (initial) d10 | d50 | d90 |
|---|---|---|---|---|---|---|---|---|---|
| 6 | 20.6 | 69.2 | 47.0 | 0.41 | 6.6 | 4.9 | 14.3 | 25.4 | 68.4 |
| 10 | 19.7 | 74.6 | 47.0 | 0.81 | 6.7 | 5.2 | 13.8 | 24.4 | 55.9 |
| 8 | 23.0 | 90.7 | 59.0 | 0.37 | 6.8 | N/A | 13.4 | 23 | 48 |

TABLE 3

Summary of PK Data for Select BUP-MVL Formulations

| Formulation | Dose (mg/kg) | $C_{max}$ (ng/mL) | $C_{max}/C_{avg}$ | $T_{max}$ (hr) | AUC/dose (ng-hr/mL/mg/kg) | Cumulative AUC % at 0-24 hours |
|---|---|---|---|---|---|---|
| 6 | 31.7 | 54 | 1.8 | 72 | 231 | 9 |
| 10 | 30.3 | 41 | 1.8 | 6 | 167 | 12 |
| 8 | 35.4 | 88 | 2.1 | 72 | 282 | 11 |

Example 4—Stability Study for Select BUP-MVL Formulations

The stability of select BUP-MVL formulations discussed herein was studied after stored at 5° C. for six months. Table 4 summarizes the six-month stability study of Formulations 6 and 10. It was observed that both formulations demonstrated excellent stability with percent free bupivacaine to be less than 0.51% and 0.73% by weight respectively.

TABLE 4

Summary of Stability Study of Select BUP-MVL Formulations

| Formulation | Total [BUP] (mg/mL) | % PPV | % Free | Ext. pH | Int. pH | PSD (initial) | | |
|---|---|---|---|---|---|---|---|---|
| | | | | | | d10 | d50 | d90 |
| 6 | 20.7 | 46 | 0.51 | 6.6 | N/A | 13.6 | 24.9 | 75.9 |
| 10 | 19.9 | 46 | 0.73 | 6.7 | N/A | 13.3 | 23.2 | 49.3 |

While the present application has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition of bupivacaine encapsulated multivesicular liposomes (MVLs), comprising:
    bupivacaine residing inside a plurality of internal aqueous chambers of the MVLs separated by lipid membranes, wherein the lipid membranes comprise DPPG or a salt thereof, DEPC, cholesterol, and a triglyceride selected from the group consisting of triolein, tricaprylin, and combinations thereof; and
    an aqueous medium in which the bupivacaine encapsulated MVLs are suspended, wherein the aqueous medium comprises at least one buffering agent in a concentration from about 1 mM to about 50 mM, and wherein the osmolality of the aqueous medium is from about 320 mOsm/kg to about 360 mOsm/kg;
    wherein the bupivacaine concentration in the composition is from about 18 mg/mL to about 40 mg/mL, and
    wherein the plurality of internal aqueous chambers of the MVLs comprises one or more pH modifying agents, and has a pH from about 3.0 to about 6.6.

2. The composition of claim 1, wherein the bupivacaine concentration in the composition is about 20 mg/mL.

3. The composition of claim 1, wherein the composition comprises less than about 2% by weight of unencapsulated bupivacaine.

4. The composition of claim 1, wherein the lipid membrane comprises DPPG, DEPC, cholesterol, tricaprylin, and triolein.

5. The composition of claim 1, wherein the one or more pH modifying agents is selected from the group consisting of organic acids, organic bases, inorganic acids, and inorganic bases, and combinations thereof.

6. The composition of claim 5, wherein the one or more pH modifying agents comprises phosphoric acid.

7. The composition of claim 1, wherein the plurality of internal aqueous chambers of the MVLs has a pH from about 3.5 to about 6.6.

8. The composition of claim 1, wherein the percent packed particle volume (% PPV) of the bupivacaine encapsulated multivesicular liposomes in the composition is about 35% to 80%.

9. The composition of claim 1, wherein the at least one buffering agent comprises sodium phosphate.

10. The composition of claim 9, wherein the concentration of sodium phosphate in the composition is from about 5 mM to about 20 mM.

11. The composition of claim 1, wherein the pH of the aqueous medium is from about 6.5 to about 7.5.

12. The composition of claim 3, wherein the increase of unencapsulated bupivacaine in the composition is less than about 5% by weight after the composition is stored at 5° C. for six months.

13. The composition of claim 1, wherein the bupivacaine is in the form of bupivacaine phosphate.

14. A method of treating or ameliorating pain in a subject in need thereof, comprising administering a composition of claim 1 to the subject.

15. The method of claim 14, wherein the administration is selected from the group consisting of infiltration, subcutaneous injection, tissue injection, intramuscular injection, spinal injection, intraocular injection, epidural injection, subarachnoid injection, sacroiliac joints injection, intrathecal injection, caudal injection, intraotic injection, and perineural injection, and combinations thereof.

16. The method of claim 14, wherein the administration is via local infiltration to a surgical site.

17. The method of claim 14, wherein the administration is via nerve block.

18. The method of claim 17, wherein the administration is via interscalene brachial plexus nerve block, femoral nerve block, sciatic nerve block, or ganglion block.

19. The method of claim 14, wherein the pain is post-surgical pain or chronic pain.

20. The method of claim 19, wherein the chronic pain comprises myofascial pain syndromes, complex regional pain syndromes, or radicular back pain.

21. The method of claim 14, wherein the Tmax of bupivacaine is from about 6 hours to about 96 hours.

22. The method of claim 14, wherein the percent AUC (0-24 hours) of bupivacaine is from about 4% to about 25%, from about 6% to about 20%, or from about 8% to about 15%.

23. The method of claim 14, wherein the total percent AUC is above 90% from 192 hours to about 216 hours post administration.

24. The method of claim 14, wherein the Cmax of bupivacaine is from about 40 ng/ml to about 100 ng/ml.

25. The method of claim 14, wherein the administration provides a sustained release of bupivacaine for about 5 to 15 days.

26. A process for preparing bupivacaine encapsulated multivesicular liposomes (MVLs), comprising:
mixing a first aqueous solution comprising one or more pH modifying agents with a lipid solution comprising at least one organic solvent, DPPG or a salt thereof, DEPC, cholesterol, and a triglyceride selected from the group consisting of triolein, tricaprylin, and combinations thereof to form a first water-in-oil emulsion, wherein at least one of the first aqueous solution and the lipid solution comprises bupivacaine;
combining the first water-in-oil emulsion with a second aqueous solution to form a second emulsion; and
substantially removing the organic solvent from the second emulsion to form a first aqueous suspension of bupivacaine encapsulated MVLs; and
exchanging the aqueous supernatant of the first aqueous suspension with a third aqueous solution one or more times to provide a final aqueous suspension of bupivacaine encapsulated MVLs, wherein the bupivacaine concentration in the final aqueous suspension is from about 18 mg/mL to about 40 mg/mL, and wherein the final aqueous suspension comprises at least one buffering agent in a concentration from about 1 mM to about 50 mM; and wherein the osmolality of the final aqueous suspension is from about 320 mOsm/kg to about 360 mOsm/kg.

27. The process of claim 26, wherein the bupivacaine concentration in the final aqueous suspension is about 20 mg/mL.

28. The process of claim 26, wherein the one or more pH modifying agents in the first aqueous solution comprises phosphoric acid.

29. The process of claim 28, wherein the molar ratio of bupivacaine to phosphoric acid in the first aqueous solution is from about 1:1.2 to about 1:2.

30. The process of claim 26, wherein the second aqueous solution comprises lysine and dextrose, and the second aqueous solution has the osmolality from about 210 mOsm/kg to about 285 mOsm/kg.

31. The process of claim 26, wherein the lipid solution comprises DPPG or a salt thereof, DEPC, cholesterol, tricaprylin, and triolein.

32. The process of claim 31, wherein the mass ratio of tricaprylin to triolein is from about 3:1 to about 25:1.

33. The composition of claim 4, wherein the mass ratio of tricaprylin to triolein is from about 3:1 to about 25:1.

34. A composition of bupivacaine encapsulated multivesicular liposomes (MVLs), comprising:
bupivacaine residing inside a plurality of internal aqueous chambers of the MVLs separated by lipid membranes, wherein the lipid membranes comprise DPPG or a salt thereof, DEPC, cholesterol, tricaprylin and triolein; and
an aqueous medium in which the bupivacaine encapsulated MVLs are suspended, wherein the aqueous medium comprises one or more buffering agents in a concentration from about 5 mM to about 20 mM, wherein the osmolality of the aqueous medium is from about 320 mOsm/kg to about 360 mOsm/kg, and the pH of the aqueous medium is from about 6.5 to about 7.5;
wherein the bupivacaine concentration in the composition is about 20 mg/mL;
wherein the plurality of internal aqueous chambers of the MVLs comprises phosphoric acid as a pH modifying agent, and has a pH from about 3.5 to about 6.6; and
wherein the mass ratio of tricaprylin to triolein in the composition is about 5:1 to about 15:1.

35. The composition of claim 34, wherein the aqueous medium comprises about 10 mM sodium phosphate.

36. The composition of claim 35, wherein the osmolality of the aqueous medium is about 330 mOsm/kg.

37. The composition of claim 34, wherein the concentration of DEPC in the composition is from about 8 mg/mL to 12 mg/ml;
the concentration of DPPG or a salt thereof in the composition is from about 0.7 mg/mL to about 1.5 mg/ml;
the concentration of cholesterol in the composition is from about 4 mg/mL to about 7 mg/mL;
the concentration of tricaprylin in the composition is from about 2 mg/mL to about 5 mg/mL; and
the concentration of triolein in the composition is about 0.3 mg/mL to about 1.0 mg/mL.

38. A method of treating or ameliorating pain in a subject in need thereof, comprising administering a composition of claim 34 to the subject by a single injection, and wherein the administration provides a sustained release of bupivacaine for 5 to 15 days.

* * * * *

UNITED STATES PATENT AND TRADEMARK OFFICE
CERTIFICATE OF CORRECTION

PATENT NO. : 12,285,419 B2
APPLICATION NO. : 18/046416
DATED : April 29, 2025
INVENTOR(S) : Louie D. Garcia et al.

It is certified that error appears in the above-identified patent and that said Letters Patent is hereby corrected as shown below:

In the Specification

Column 2, Line 52, delete "90 km. In" and insert -- 90 μm. In --.

Column 2, Line 54, delete "80 m, about" and insert -- 80 μm, about --.

Column 2, Line 55, delete "70 km." and insert -- 70 μm. --.

Column 10, Line 62, delete "first and or the" and insert -- first and/or the --.

Column 11, Line 37, delete "30 m, 35" and insert -- 30 μm, 35 --.

Column 14, Line 8, delete "of the the second" and insert -- of the second --.

Column 16, Line 18, delete "as phosphotidylcholine or phosphotidylgycerol or" and insert -- as phosphatidylcholine or phosphatidylglycerol or --.

In the Claims

Column 25, Line 2, Claim 24, delete "40 ng/ml to" and insert -- 40 ng/mL to --.

Column 25, Line 2, Claim 24, delete "100 ng/ml." and insert -- 100 ng/mL. --.

Column 26, Line 32 (approx.), Claim 37, delete "12 mg/ml;" and insert -- 12 mg/mL; --.

Column 26, Line 34 (approx.), Claim 37, delete "1.5 mg/ml;" and insert -- 1.5 mg/mL; --.

Signed and Sealed this
Eighth Day of July, 2025

Coke Morgan Stewart
*Acting Director of the United States Patent and Trademark Office*